(12) United States Patent
Flaherty et al.

(10) Patent No.: US 7,647,097 B2
(45) Date of Patent: Jan. 12, 2010

(54) TRANSCUTANEOUS IMPLANT

(75) Inventors: J. Christopher Flaherty, Topsfield, MA (US); K. Shane Guillory, Salt Lake City, UT (US); Mijail D. Serruya, Providence, RI (US); Abraham H. Caplan, Cambridge, MA (US)

(73) Assignee: BrainGate Co., LLC, Ponte Verdra Beach, FL (US)

( * ) Notice: Subject to any disclaimer, the term of this patent is extended or adjusted under 35 U.S.C. 154(b) by 967 days.

(21) Appl. No.: 11/014,907

(22) Filed: Dec. 20, 2004

(65) Prior Publication Data

US 2005/0283203 A1 Dec. 22, 2005

Related U.S. Application Data

(60) Provisional application No. 60/532,984, filed on Dec. 29, 2003.

(51) Int. Cl.
*A61B 5/04* (2006.01)

(52) U.S. Cl. ........................ 600/544; 600/545

(58) Field of Classification Search ................ 600/372, 600/373, 377, 378, 544, 545
See application file for complete search history.

(56) References Cited

U.S. PATENT DOCUMENTS

| | | | |
|---|---|---|---|
| 662,998 A * | 12/1900 | Wright et al. .............. | 396/372 |
| 3,837,339 A | 9/1974 | Aisenberg et al. | |
| 3,850,161 A | 11/1974 | Liss | |
| 4,055,175 A | 10/1977 | Clemens et al. | |
| 4,146,029 A | 3/1979 | Ellinwood, Jr. | |
| 4,294,245 A | 10/1981 | Bussey | |
| 4,360,031 A | 11/1982 | White | |
| 4,461,304 A | 7/1984 | Kuperstein | |
| 4,633,889 A | 1/1987 | Talalla et al. | |
| 4,690,142 A | 9/1987 | Ross et al. | |
| 4,837,049 A | 6/1989 | Byers et al. | |

(Continued)

FOREIGN PATENT DOCUMENTS

WO    WO 01/43635    6/2001

(Continued)

OTHER PUBLICATIONS

Kensall D. Wise et al., "An Integrated-Circuit Approach to Extraceullar Microelectrodes," IEEE Transactions on Biomedical Engineering, vol. BME-17, No. 3, Jul. 1970, pp. 238-247.

(Continued)

*Primary Examiner*—Patricia C Mallari
*Assistant Examiner*—Karen E Toth
(74) *Attorney, Agent, or Firm*—SoCal IP Law Group LLP; Steven C. Sereboff; M. Kala Sarvaiya

(57) ABSTRACT

Devices, systems and methods are disclosed for a neural access device that includes an implant which transcutaneously exits the skin of a patient and provides transport of signals between a sensor implanted in a patient and an external device. The transcutaneous implant has integrated features to provide reduced risk of injury due to mechanical forces as well as electrostatic discharge energy applied to the external portion of the device. Transcutaneous devices which provide wireless communication between a sensor and an external device are also disclosed.

64 Claims, 6 Drawing Sheets

U.S. PATENT DOCUMENTS

| | | | |
|---|---|---|---|
| 4,865,048 A | 9/1989 | Eckerson | |
| 4,878,913 A | 11/1989 | Aebischer et al. | |
| 4,883,666 A | 11/1989 | Sabel et al. | |
| 4,936,306 A * | 6/1990 | Doty | 600/373 |
| 4,969,468 A | 11/1990 | Byers et al. | |
| 5,026,397 A | 6/1991 | Aoki et al. | |
| 5,037,376 A | 8/1991 | Richmond et al. | |
| 5,081,990 A | 1/1992 | Deletis | |
| 5,119,832 A | 6/1992 | Xavier | |
| 5,156,844 A | 10/1992 | Aebischer et al. | |
| 5,215,088 A | 6/1993 | Normann et al. | |
| 5,325,865 A | 7/1994 | Beckman et al. | |
| 5,355,883 A * | 10/1994 | Ascher | 600/394 |
| 5,361,760 A | 11/1994 | Normann et al. | |
| 5,423,877 A | 6/1995 | Mackey | |
| 5,445,608 A | 8/1995 | Chen et al. | |
| 5,458,631 A | 10/1995 | Xavier | |
| 5,474,547 A | 12/1995 | Aebischer et al. | |
| 5,584,870 A * | 12/1996 | Single et al. | 607/63 |
| 5,617,871 A | 4/1997 | Burrows | |
| 5,638,826 A | 6/1997 | Wolpaw et al. | |
| 5,687,291 A | 11/1997 | Smyth | |
| 5,689,137 A * | 11/1997 | Weber | 257/679 |
| 5,692,517 A | 12/1997 | Junker | |
| 5,697,951 A | 12/1997 | Harpstead et al. | |
| 5,702,432 A | 12/1997 | Chen et al. | |
| 5,713,923 A | 2/1998 | Ward et al. | |
| 5,735,885 A | 4/1998 | Howard, III et al. | |
| 5,758,651 A | 6/1998 | Nygard et al. | |
| 5,782,645 A | 7/1998 | Stobie et al. | |
| 5,797,898 A | 8/1998 | Santini, Jr. et al. | |
| 5,814,089 A | 9/1998 | Stokes et al. | |
| 5,843,093 A | 12/1998 | Howard, III | |
| 5,843,142 A | 12/1998 | Sultan | |
| 5,855,801 A | 1/1999 | Lin et al. | |
| 5,873,368 A | 2/1999 | Sabin | |
| 5,873,840 A | 2/1999 | Neff | |
| 5,928,228 A | 7/1999 | Kordis et al. | |
| 5,938,688 A | 8/1999 | Schiff | |
| 5,938,689 A | 8/1999 | Fischell et al. | |
| 5,938,690 A | 8/1999 | Law et al. | |
| 6,001,065 A | 12/1999 | DeVito | |
| 6,006,124 A | 12/1999 | Fischell et al. | |
| 6,016,449 A | 1/2000 | Fischell et al. | |
| 6,024,700 A | 2/2000 | Nemirovski et al. | |
| 6,024,702 A | 2/2000 | Iversen | |
| 6,027,456 A | 2/2000 | Feler et al. | |
| 6,038,477 A | 3/2000 | Kayyali | |
| 6,061,593 A | 5/2000 | Fischell et al. | |
| 6,086,582 A | 7/2000 | Altman et al. | |
| 6,091,015 A | 7/2000 | del Valle et al. | |
| 6,091,979 A * | 7/2000 | Madsen | 600/377 |
| 6,092,058 A | 7/2000 | Smyth | |
| 6,113,553 A | 9/2000 | Chubbuck | |
| 6,125,300 A | 9/2000 | Weijand et al. | |
| 6,128,538 A | 10/2000 | Fischell et al. | |
| 6,134,474 A | 10/2000 | Fischell et al. | |
| 6,154,678 A | 11/2000 | Lauro | |
| 6,161,045 A | 12/2000 | Fischell et al. | |
| 6,163,725 A | 12/2000 | Peckham et al. | |
| 6,169,981 B1 | 1/2001 | Werbos | |
| 6,171,239 B1 * | 1/2001 | Humphrey | 600/372 |
| 6,175,762 B1 | 1/2001 | Kirkup et al. | |
| 6,181,965 B1 | 1/2001 | Loeb et al. | |
| 6,185,455 B1 | 2/2001 | Loeb et al. | |
| 6,216,045 B1 | 4/2001 | Black et al. | |
| 6,224,549 B1 | 5/2001 | Drongelen | |
| 6,240,315 B1 | 5/2001 | Mo et al. | |
| 6,254,536 B1 | 7/2001 | DeVito | |
| 6,263,237 B1 | 7/2001 | Rise | |
| 6,280,394 B1 | 8/2001 | Maloney et al. | |
| 6,309,410 B1 | 10/2001 | Kuzma et al. | |
| 6,313,093 B1 | 11/2001 | Frey, II | |
| 6,319,241 B1 | 11/2001 | King et al. | |
| 6,330,466 B1 * | 12/2001 | Hofmann et al. | 600/378 |
| 6,353,754 B1 | 3/2002 | Fischell et al. | |
| 6,354,299 B1 | 3/2002 | Fischell et al. | |
| 6,356,784 B1 | 3/2002 | Lozano et al. | |
| 6,358,202 B1 | 3/2002 | Arent | |
| 6,360,122 B1 | 3/2002 | Fischell et al. | |
| 6,366,813 B1 | 4/2002 | DiLorenzo | |
| 6,427,086 B1 | 7/2002 | Fischell et al. | |
| 6,436,708 B1 | 8/2002 | Leone et al. | |
| 6,459,936 B2 | 10/2002 | Fischell et al. | |
| 6,466,822 B1 | 10/2002 | Pless | |
| 6,473,639 B1 | 10/2002 | Fischell et al. | |
| 6,474,080 B2 * | 11/2002 | Varone et al. | 62/55.5 |
| 6,480,743 B1 | 11/2002 | Kirkpatrick et al. | |
| 6,503,228 B1 | 1/2003 | Li et al. | |
| 6,577,893 B1 | 6/2003 | Besson et al. | |
| 6,593,794 B2 * | 7/2003 | Yue et al. | 327/310 |
| 6,606,521 B2 * | 8/2003 | Paspa et al. | 607/116 |
| 6,620,415 B2 | 9/2003 | Donovan | |
| 6,900,970 B2 * | 5/2005 | Miller et al. | 361/56 |
| 6,973,342 B1 * | 12/2005 | Swanson | 600/378 |
| 2001/0008972 A1 * | 7/2001 | Gielen | 607/45 |
| 2001/0023368 A1 | 9/2001 | Black et al. | |
| 2001/0027336 A1 | 10/2001 | Gielen et al. | |
| 2001/0029391 A1 | 10/2001 | Gluckman et al. | |
| 2001/0051819 A1 | 12/2001 | Fischell et al. | |
| 2001/0056290 A1 | 12/2001 | Fischell et al. | |
| 2002/0002390 A1 | 1/2002 | Fischell et al. | |
| 2002/0013612 A1 | 1/2002 | Whitehurst | |
| 2002/0016638 A1 | 2/2002 | Mitra et al. | |
| 2002/0028991 A1 * | 3/2002 | Thompson | 600/372 |
| 2002/0049451 A1 * | 4/2002 | Parmer et al. | 606/108 |
| 2002/0077620 A1 | 6/2002 | Sweeney et al. | |
| 2002/0099412 A1 | 7/2002 | Fischell et al. | |
| 2002/0161403 A1 | 10/2002 | Meadows et al. | |
| 2002/0169485 A1 | 11/2002 | Pless et al. | |
| 2003/0004428 A1 | 1/2003 | Pless et al. | |
| 2003/0074032 A1 | 4/2003 | Gliner | |
| 2003/0078592 A1 * | 4/2003 | Heilman et al. | 606/108 |
| 2003/0082507 A1 | 5/2003 | Stypulkowski | |
| 2003/0083716 A1 | 5/2003 | Nicolelis et al. | |
| 2003/0083724 A1 | 5/2003 | Jog et al. | |
| 2003/0093129 A1 | 5/2003 | Nicolelis et al. | |
| 2004/0006264 A1 | 1/2004 | Majarradi et al. | |
| 2004/0006281 A1 * | 1/2004 | Matsukawa et al. | 600/544 |
| 2004/0010208 A1 * | 1/2004 | Ayad | 600/587 |
| 2004/0133118 A1 * | 7/2004 | Llinas | 600/544 |
| 2004/0138579 A1 | 7/2004 | Deadwyler et al. | |
| 2004/0162586 A1 * | 8/2004 | Covey et al. | 607/5 |
| 2004/0267153 A1 * | 12/2004 | Bergethon | 600/554 |
| 2004/0267320 A1 | 12/2004 | Taylor et al. | |

FOREIGN PATENT DOCUMENTS

| | | |
|---|---|---|
| WO | WO 01/60445 | 8/2001 |
| WO | WO 03/026739 | 4/2003 |
| WO | WO 03/035165 | 5/2003 |
| WO | WO 03/037231 | 5/2003 |
| WO | WO 03/101532 | 12/2003 |

OTHER PUBLICATIONS

Donald R. Humphrey et al., "Predicting Measures of Motor Performance from Multiple Cortical Spike Trains," Science, New Series, vol. 170, Issue 3959, Nov. 13, 1970, pp. 758-762.

A. Bohg, "Ethylene Diamine-Pyrocatechol-Water Mixture Shows Etching Anomaly in Boron-Doped Silicon," Journal of the Electrochemical Society, vol. 118, No. 2, Feb. 1971, pp. 401-402.

Donald R. Humphrey, "Relating Motor Cortex Spike Trains to Measures of Motor Performance," Department of Physiology, Emory University, Brain Research, No. 40, 1972, pp. 7-18.

Arnold Starr et al., "An Evaluation of Photoengraved Microelectrodes for Extracellular Single-Unit Recording," IEEE Transactions on Biomedical Engineering, vol. BME-20, No. 4, Jul. 1973, pp. 291-293.

Kensall D. Wise et al., "A Low-Capacitance Multielectrode Probe for Use in Extracellular Neurophysiology," IEEE Transactions on Biomedical Engineering, vol. BME-22, No. 3, May 1975, pp. 212-219.

V. B. Mountcastle et al., "Posterior Parietal Association Cortex of the Monkey: Command Functions for Operations Within Extrapersonal Space," The Journal of Neurophysiology, vol. 38, No. 4, 1975, pp. 871-908.

Edward M. Schmidt, "Single Neuron Recording From Motor Cortex as a Possible Source of Signals for Control of External Devices," Annals of Biomedical Engineering, vol. 8, 1980, pp. 339-349.

A. J. S. Summerlee et al., "The effect of behavioural arousal on the activity of hypothalamic neurons in unanaesthetized, freely moving rats and rabbits," Proceedings of the Royal Society of London Series B-Biological Sciences, Jan. 1982, pp. 263-272.

Spencer L. BeMent, et al., "Solid-State Electrodes for Multichannel Multiplexed Intracortical Neuronal Recording," IEEE Transactions on Biomedical Engineering, vol. BME-33, No. 2, Feb. 1986, pp. 230-241.

Camilo Toro et al., "8-12 Hz rhythmic oscillations in human motor cortex during two-dimensional arm movements: evidence for representation of kinematic parameters," Departments of Neurology, Neurosurgery, and Physiology, University of Minnesota; MINCEP Epilepsy Care, P.A.; The Minessota Epilepsy Group of United and St. Paul Children's Hospital; and Human Motor Control Section, National Institute of Neurological Disorders and Stroke, National Institutes of Health, Electoencephaloraphy and Clinical Neurophysiology, No. 93, 1994, pp. 390-403.

Anthony L. Owens et al., "Multi-electrode array for measuring evoked potentials from surface of ferret primary auditory cortex," Journal of Neuroscience Methods, vol. 58, Nos. 1/2, May 1995, pp. 209-220.

Miguel A. L. Nicolelis et al., "Sensorimotor Encoding by Synchronous Neural Ensemble Activity at Multiple Levels of the Somatosensory System," Science, vol. 268, Jun. 2, 1995, pp. 1353-1358.

Jerome N. Sanes et al., "Shared Neural Substrates Controlling Hand Movements in Human Motor Cortex," Science, vol. 268, Jun. 23, 1995, pp. 1775-1777.

D.M. Halliday et al., "A Framework for the Analysis of Mixed Time Series/Point Process Data-Theory and Application to the Study of Physiological Tremor, Single Motor Unit Discharges and Electromyograms," Progress in Biophysics Molecular Biology, vol. 64, Nos. 2/3, 1995, pp. 237-278.

Qing Bai et al., "A High-Yield Process for Three-Dimensional Microelectrode Arrays," Solid-State Sensor and Actuator Workshop, Hilton Head, South Carolina, Jun. 2-6, 1996, pp. 262-265.

Apostolos P. Georgopoulos et al., "Neuronal Population Coding of Movement Direction," Science, vol. 233, Sep. 26, 1986, pp. 1416-1419.

Kenneth L. Drake et al., "Performance of Planar Multisite Microprobes in Recording Extracellular Single-Unit Intracortical Activity," IEEE Transactions on Biomedical Engineering, vol. 35, No. 9, Sep. 1988, pp. 719-732.

Patrick K. Campbell et al., "A chronic intracortical electrode array: Preliminary results," Journal of Biomed. Material Res.: Applied Biomaterials, vol. 23, No. 2, 1989, pp. 245-259.

Andrew R. Mitz et al., "Learning-dependent Neuronal Activity in the Premotor Cortex: Activity during the Acquisition of Conditional Motor Associations," The Journal of Neuroscience, vol. 11, No. 6, Jun. 1991, pp. 1855-1872.

Patrick K. Campbell et al., "A Silicon-Based, Three-Dimensional Neural Interface: Manufacturing Processes for an Intracortical Electrode Array," IEEE Transactions, 1991, pp. 758-768.

A. C. Hoogerwerf et al., "A Three-Dimensional Neural Recording Array," IEEE Transactions, 1991, pp. 120-123.

Gregory T. A. Kovacs et al., "Regeneration Microelectrode Array for Peripheral Nerve Recording and Stimulation," Transactions on Biomedical Engineering, vol. 39, No. 9, Sep. 1992, pp. 893-902.

Kelly E. Jones et al., "A Glass/Silicon Composite Intracortical Electrode Array," Annals of Biomedical Engineering. vol. 20, 1992, pp. 423-437.

Miguel A. L. Nicolelis et al., "Induction of immediate spatiotemporal changes in thalamic networks by peripheral block of ascending cutaneous information," Letters to Nature, vol. 361, Feb. 11, 1993, pp. 533-536.

Reinhard Eckhorn et al., "A new method for the insertion of multiple microprobes into neural and muscular tissue, including fiber electrodes, fine wires, needles and microsensors," Journal of Neuroscience Methods, vol. 49, Nos. 1/2, 1993, pp. 175-179.

Craig T. Nordhausen et al., "Optimizing recording capabilities of the Utah Intracortical Electrode Array," Brain Research, vol. 637, Nos. 1/2, Feb. 21, 1994, pp. 27-36.

Jamille F. Hetke et al., "Silicon Ribbon Cables for Chronically Implantable Microelectrode Arrays," IEEE Transactions on Biomedical Engineering, vol. 41, No. 4, Apr. 1994, pp. 314-321.

Miguel A. L. Nicolelis et al., "Spatiotemporal Structure of Somatosensory Responses of Many-Neuron Ensembles in the Rat Ventral PosteriorMedial Nucleus of the Thalamus," The Journal of Neuroscience, vol. 14, No. 6, Jun. 1994, pp. 3511-3532.

Arnold C. Hoogerwerf et al., "A Three-Dimensional Microelectrode Array for Chronic Neural Recording," IEEE Transactions on Biomedical Engineering, vol. 41, No. 12, Dec. 1994, pp. 1136-1146.

Changhyun Kim et al., "A 64-Site Multishank CMOS Low-Profile Neural Stimulating Probe," IEEE Journal of Solid-State Circuits, vol. 31, No. 9, Sep. 1996, pp. 1230-1238.

Gwo-Ching Chang et al., "Real-time implementation of electromyogram pattern recognition as a control command of man-machine interface," Medical Engineering Phys., vol. 18, No. 7, 1996, pp. 529-537.

P. Nisbet, "intergrating assistive technologies: current practices and future possibilities," Med. Eng. Phys., vol. 18, No. 3, 1996, pp. 193-202.

Miguel A. L. Nicolelis et al., "Reconstructing the Engram: Simultaneous, Multisite, Many Sinle Neuron Recordings," Nueron, vol. 18, Apr. 1997, pp. 529-537.

TR Scott et al., "The Monitoring of Tendon Tension with an Implantable Intratendon Probe and Its Use in the Control of Neuroprostheses," IEEE Transactions on Rehabilitation Engineering, vol. 5, No. 2, Jun. 1997, pp. 233-235.

Barbara M. Faggin et al., "Immediate and simultaneous sensory reorganization at cortical and subcortical levels of the somatosensory system," Proc. Natl. Acad. Science USA, vol. 94, Aug. 1997, pp. 9428-9433.

Nicolelis, Miguel A.L., "Trigeminal System Plasticity During Facial Anethesia," Department of Health and Human Services, Public Health Service, Grant No. 2 R01 DE11451-05, Including Summary Statement, Oct. 1997.

Robert M. Bradley et al., "Long term chronic recordings from peripheral sensory fibers using a sieve electrode array," Journal of Neuroscience Methods, vol. 73, 1997, pp. 177-186.

David K. Warland et al., "Decoding Visual Information From a Population of Retinal Ganglion Cells," The American Physiological Society, 1997, pp. 2336-2350.

Steven P. Wise et al., "Premotor and Parietal Cortex: Cortiococortical Connectivity and Combinatorial Computations," Annual Review of Neuroscience, vol. 20, 1997, pp. 25-42.

P.R. Kennedy et al., "Restoration of neural output from a paralyzed patient by a direct brain connection," NeuroReport, vol. 9, No. 8, Jun. 1998 pp. 1707-1711.

Paolo Dario et al., "Neural Interfaces for Regenerated Nerve Stimulation and Recording," IEEE Transactions on Rehabilitation Engineering, vol. 6, No. 4, Dec. 1998, pp. 353-363.

Nicholas G. Hatsopoulos et al., "Information about movement direction obtained from synchronous activity of motor cortical neurons," Proc. Natl. Acad. Sci. USA, vol. 95, Dec. 1998, pp. 15706-15711.

John P. Donoghue et al., "Neural Discharge and Local Field Potential Oscillations in Primate Motor Cortex During Voluntary Movements," The American Physiological Society, 1998, pp. 159-173.

Nicolelis, Miguel A.L., "Trigeminal System Plasticity During Facial Anethesia," Department of Health and Human Services, Public Health Service, Grant No. 2 R01 DE11451-06, Apr. 1999.

Gregor Rainer et al., "Prospective Coding for Objects in Primate Prefrontal Cortex," The Journal of Neuroscience, vol. 19, No. 13, Jul. 1, 1999, pp. 5493-5505.

John K. Chapin et al., "Real-time control of a robot arm using simultaneously recorded neurons in the motor cortex," Department of Neurobiology and Anatomy, MCP Hahnemann School of Medicine; and Department of Neurobiology, Duke University Medical Center, Nature Neuroscience, vol. 2, No. 7, Jul. 1999, pp. 664-670.

E. M. Maynard et al, "Neuronal Interactions Improve Cortical Population Coding of Movement Direction," The journal of Neuroscience, vol. 19, No. 18, Sep. 15, 1999, pp. 8083-8093.

F. Gandolfo et al., "Cortical correlates of learning in monkeys adapting to a new dynamical environment," PNAS, vol. 97, No. 5, Feb. 29, 2000, pp. 2259-2263.

J. F. Marsden et al., "Organization of Cortical Activities Related to Movement in humans," The Journal of Neuroscience, vol. 20, No. 6, Mar. 15, 2000, pp. 2307-2314.

D. Gareth Evans et al., "Controlling mouse Pointer Position Using an Infrared Head-Operated Joystick," IEEE Transaction on Rehabilitation Engineering, vol. 8, No. 1, Mar. 2000, pp. 107-117.

Qing Bai et al., "A High-Yield Microassembly Structure For Three-Dimensional Microelectrode Arrays," IEEE Transactions on Biomedical Engineering, vol. 47, No. 3, Mar. 2000, pp. 281-289.

Nicolelis, Miguel A.L., "Trigeminal System Plasticity During Facial Anethesia," Department of Health and Human Services, Public health Service, Grant No. 2 R01 DE11451-07, Apr. 2000.

Nicolelis, Miguel A.L., "Corticofugal Modulation of Tactile Sensory Processing," Department of Health and Human Services, Public Health Service, National Institute of Dental and Craniofacial Research of the Nationsl Institutes of health, Grant No. 1 R01 DE013810-01 A1, Jun. 2000.

Jonathan R. Wolpaw et al., "Brain-Computer Interface Technology: A Review of the First International Meeting," IEEE Transactions on Rehabilitation Engineering, vol. 8, No. 2, Jun. 2000, pp. 164-173.

Simon P. Levine et al., "A Direct Brain Interface Based on Event-Related potentials," IEEE Transactions on Rehabilitation Engineering, vol. 8, No. 2, Jun. 2000, pp. 180-185.

Robert E. Isaacs et al., "Work Toward Real-Time Control of a cortical Neural Prothesis," IEEE Transactions on Rehabilitation Engineering, vol. 8, No. 2, Jun. 2000, pp. 196-198.

Scott Makeig et al., A Natural Basis for Efficient Brain-Actuated Control, IEEE Transactions on Rehabilitation Engineering, vol. 8, No. 2, Jun. 2000, pp. 208-211.

Johan Wessberg et al., "Real-time prediction of hand trajectory by ensembles of cortical neurons in primates," Nature, vol. 408, Nov. 16, 2000, pp. 361-365.

Jerome N. Sanes et al., "Plasticity and Primary Motor Cortex," Annual Reviews, Neuroscience, Brown University, Library, vol. 23, 2000, pp. 393-415.

Jonathan C. Jarvis et al., "The application and technology of implantable neuromuscular stimulators: an introduction and overview," Medical Engineering & Physics, No. 23, Jan. 11, 2001, pp. 3-7.

Miguel A. L. Nicolelis, "Real-time direct interfaces between the brain and electronic and mechanical devices could one day be used to restore sensory and motor functions lost through injury or disease. Hybrid brain-machine interfaces also have the potential to enhance our perceptual, motor and cognitive capabilities by revolutionizing the way we use computers and interact with remote environments," Nature, vol. 409, Jan. 18, 2001, pp. 403-407.

Gerald E. Loeb et al., "BION™ system for distributed neural prosthetic interfaces," Medical Engineering & Physics, vol. 23, Jan. 26, 2001, pp. 9-18.

Patrick J. Rousche et al., "Flexible Polyimide-Based Intracortical Electrode Arrays with Bioactive Capability," IEEE Transactions on Biomedical Engineering, vol. 48, No. 3, Mar. 2001, pp. 361-371.

Nicolelis, Miguel A.L., "Trigeminal System Plasticity During Facial Anethesia," Department of Health and Human Services, Public Health Service, Grant No. 2 R01 DE11451-08, Apr. 2001.

Qing Bai et al., "Single-Unit Neural Recording with Active Microelectrode Arrays," IEEE Transactions on Biomedical Engineering, vol. 48, No. 8, Aug. 2001, pp. 911-920.

David L. Zealear et al., "The Biocompatibility, Integrity, and Positional Stability of an Injectable Microstimulator for Reanimation of the Paralyzed Larynx," IEEE Transactions on Biomedical Engineering, vol. 48, No. 8, Aug. 2001, pp. 890-897.

Dawn M. Taylor et al., "Using Virtual Reality to Test the Feasibility of Controlling an Upper Limb Fes System Directly from Multiunit Activity in the Motor Cortex," Arizona State University; and The Neurosciences Institute, Summer 2001, pp. 1-3.

Ranu Jung et al., "Real-Time Interaction Between a Neuromorphic Electronic Circuit and the Spinal Cord," IEEE Transactions on Neural Systems and Rehabilitation Engineering, vol. 9, No. 3, Sep. 2001, pp. 319-326.

Shay Shoham, "Advances Towards an Implantable Motor Cortical Interface," The University of Utah, Dec. 2001, pp. 1-157.

John K. Chapin et al., "Neural Prostheses for Restoration of Sensory and Motor Function," CRC Press, LLC, 2001, Chapters 6, 8 and 9 pp. 179-219, pp. 235-261, pp. 263-283.

Andrew B. Schwartz et al., "Extraction algorithms for cortical control of arm prosthetics," The Neuroscience Institute; and Department of Bioengineering, Arizona State University, 2001, pp. 701-707.

István Ulbert et al., "Multiple microelectrode-recording system for human intracortical applications," Journal of Neuroscience Methods, vol. 106, 2001, pp. 69-79.

Mijail D. Serruya et al., "Instant Neural Control of a Movement Signal," Nature, vol. 416, Mar. 14, 2002, pp. 141-142.

Nicolelis, Miguel A.L., "Corticofugal Modulation of Tactile Sensory Processing," Department of Health and Human Services, Public health Service, National Institute of Dental and Craniofacial Research of the Nationsl Institutes of Health, Grant No. 5 R01 DE013810-02, Mar. 2002.

Nicolelis, Miguel A.L., "Trigeminal System Plasticity During Facial Anethesia," Department of Health and Human Services, Public Health Service, Grant No. 2 R01 DE11451-09, Apr. 2002.

Dawn M. Taylor et al., "Direct Cortical Control of 3D Neuroprosthetic Devices," Science, vol. 296, Jun. 7, 2002, pp. 1829-1832.

John P. Donoghue, "Connecting cortex to machines: recent advances in brain interfaces," Nature Neuroscience Supplement, vol. 5, Nov. 2002, pp. 1085-1088.

Y. Gao, et al., "Probabilistic Inference of Hand Motion from Neural Activity in Motor Cortex," In Advances in Neural Information Processing Systems 14, The MIT Press, 2002, pp. 1-8.

Mijail Serruya et al., "Robustness of neuroprosthetic decoding algorithms," Biological Cybernetics, 2003, pp. 1-10.

Frank Wood et al., "On the Variability of Manual Spike Sorting," Brown University, Providence, RI, Jul. 1, 2003, pp. 1-19.

Wei Wu et al., "Modeling and Decoding Motor Cortical Activity using a Switching Kalman Filter," Brown University, Providence, RI, Jul. 1, 2003, pp. 1-30.

Jose M. Carmena et al., "Learning to Control a Brain-Machine Interface for Reaching and Grasping by Primates," PLOS Biology, vol. 1, Issue 2, Oct. 13, 2003, pp. 1-16.

Nicolelis, Miguel A.L., "Brain-machine Interfaces to Restore Motor Function and Probe Neural Circuits," Nature Reviews, Neuroscience, vol. 4, May 2003, pp. 417-422.

Libet, Benjamin, "Unconscious Cerebral Initiative and the Role of Conscious Will in Voluntary Action," The Behavioral and Brain Sciences 1995) 8, pp. 529-566.

* cited by examiner

TRANSCUTANEOUS IMPLANT

This application claims the benefit of priority under 35 U.S.C. § 119(e) of U.S. provisional application no. 60/532,984, filed Dec. 29, 2003.

DESCRIPTION OF THE INVENTION

1. Field of the Invention

The present invention relates to implants that have a portion which transcutaneously exits the skin of a patient, and, more particularly, to systems, devices and methods whereby a neural interface system including multiple electrodes is connected to a transcutaneous implant. The transcutaneous implant provides a connection point which allows communication between the electrodes and an external device.

2. Description of Related Art

It is well known that messages are transmitted throughout the nervous system by means of electrical signals. Electrical signals are generated by various parts of the body, such as the sensory organs, and are transmitted to the brain. The brain in turn generates electrical signals to control muscular and other activity. Certain devices including a plurality of electrodes have been developed to electrically interface with neural tissue to either receive messages from or send signals to neural cells called neurons. These devices and other similar multi-electrode devices can be implanted in various locations within a patient's body to provide access to numerous types of living cells. Electrical connections are provided from a location accessible outside the patient's body to the electrodes, such as by way of a wire running to each electrode.

Neural interface systems are currently under development for numerous applications including restoration of lost function due to traumatic injury or neurological disease. Sensors, such as electrode arrays, implanted in the higher brain regions that control voluntary movement, can be activated voluntarily by the patient to generate electrical signals that can be processed by the neural interface system to create a thought-invoked control signal. Such control signals can be used to control numerous devices including computers and communication devices, external prostheses, such as an artificial arm, as well as robots and other remote control devices. Patient's afflicted with amyotrophic lateral sclerosis (Lou Gehrig's Disease), particularly those in advanced stages of the disease, would also be applicable to receiving a neural interface system, even if just to improve communication to the external world and thus improve their quality of life.

In various research activities, electrode arrays are placed in the motor cortex of a mammal, such as a monkey, in order to investigate the requirements of a brain-machine interface. The array is connected by way of a multi-conductor cable to a transcutaneous connector constructed of bio-compatible metal mounted to the skull of the animal. The transcutaneous connector exits through the skin above the skull, and provides a number of exposed electrically conductive pads which are used to complete a multi-signal electrical connection to a mating receptacle device. When implanted, the transcutaneous connector extends well above the skin, with the exposed portion including external threads that are used to attach to the receptacle. The extending portion creates various issues due primarily to its length and rigidity. In addition to potential damage and discomfort, the undesired visual appearance creates numerous drawbacks which will hinder acceptance of the technology for human clinical applications.

Commercialization of neural interface systems has been extremely limited, with the majority of advances made by universities in a preclinical research setting. As the technologies advance and mature, the natural progression will be to sophisticated human applications, such as those types of devices regulated by various governmental regulatory agencies including the Food and Drug Administration in the United States. When sophisticated neural interface systems are commercially available for prescription by an appropriate clinician, it will become very important for these devices to meet numerous patient and clinician requirements for performance, safety, cosmetics, and other patient needs normally exhibited by products found in hospitals and home health care settings.

There is a need for a neural interface system that includes multi-electrode arrays and transcutaneous connectors that are safer and more comfortable and that have better aesthetics or are less conspicuous. There is also a need for devices including multi-electrode arrays and transcutaneous connectors that provide one or more additional functions, thus reducing the complexities of the systems to which they are connected, or improving the performance or capabilities of those systems.

SUMMARY OF THE INVENTION

According to a first aspect of the invention, a neural access device is disclosed. The neural access device is implanted in a patient, and includes a transcutaneous connector including an external portion that provides at least one signal communication port for transport of signals between one or more electrodes and an external device. The neural access device comprises a sensor, an electrical conduit and a connector assembly. The sensor includes a plurality of electrodes that allow chronic access to various living cells of the patient. The electrical conduit comprises a plurality of conductors, and each conductor is electrically connected to one or more electrodes. The connector assembly includes a first portion configured to be placed above the surface of the skin of the patient, a second portion configured to be placed beneath the surface of the skin of the patient, attachment means for securing the second portion under the surface of the skin of the patient, and the at least one signal communication port. The neural access device according one aspect of the invention further includes means of protecting the patient from injury due to electrostatic discharge.

According to another aspect of the invention, a protective cap is included with the connector assembly to isolate or shunt the electrostatic discharge energy. The cap may be attached to the connector assembly such as to automatically cover the signal communication ports when a mating connector from an external device is not connected. The connector assembly and cap are designed to be low-profile and inconspicuous. In a preferred embodiment, real or artificial human hair is attached to the cap to camouflage the presence of transcutaneous connector assembly. Electrostatic protection means integrated into the connector assembly, as an alternative or in addition to the protective cap can be included to prevent injury due to electrostatic energy brought in proximity to the connector assembly by an operator.

In another preferred embodiment, a low-profile neural access device is disclosed. The neural access device is implanted in a patient, and includes a transcutaneous connector including an external portion that provides at least one signal communication port for transport of signals between one or more electrodes and an external device. The neural access device comprises a sensor, an electrical conduit and a connector assembly. The sensor includes a plurality of electrodes that allow chronic access to various living cells of the patient. The electrical conduit comprises of a plurality of conductors, and each conductor is electrically connected to one or more electrodes. The connector assembly includes a first portion configured to be placed above the surface of the skin of the patient, a second portion configured to be placed beneath the surface of the skin of the patient, attachment means for securing the second portion under the surface of the skin of the patient, and the at least one signal communication port. The neural access device further includes engagement means, located at least partially beneath the plane of the surface of the patient's skin, when the neural access device is implanted in the patient. The engagement means can take various forms including internal or external threads, a bayonet locking mechanism, magnetic locks and releasable latching mechanisms.

In another preferred embodiment, a neural access device with an integrated function module is disclosed. The neural access device is implanted in a patient, and includes a transcutaneous connector including an external portion that provides at least one signal communication port for transport of signals between one or more electrodes and an external device. The neural access device comprises a sensor, an electrical conduit, and a connector assembly. The sensor includes a plurality of electrodes that allow chronic access to various living cells of the patient. The electrical conduit comprises a plurality of conductors, and each conductor is electrically connected to one or more electrodes. The connector assembly includes a first portion configured to be placed above the surface of the skin of the patient, a second portion configured to be placed beneath the surface of the skin of the patient, attachment means for securing said second portion under the surface of the skin of the patient, and the at least one signal communication port. The neural access device further includes an integrated function module for performing one or more of the following functions: signal processing, signal selection, supply of power, memory storage and wireless transmission of signals or information.

In a preferred embodiment of the invention, the integrated function module performs wireless transmission of signals or information, and the information can include stimulation information received from an external device, or multicellular activity detected by the electrodes and sent to an external device. In another preferred embodiment of the invention, the integrated function module performs signal processing such as amplification, signal selection, signal deselection, signal multiplexing, setting an amplitude threshold, setting a sampling rate, setting filtering parameters, setting amplification levels and other signal conditioning techniques. In another preferred embodiment of the invention, the integrated function module performs a supply of power function. In another preferred embodiment, the integrated function module performs a memory storage function.

In another preferred embodiment, a neural access device with an attachable electrical conduit. The neural access device is implanted in a patient, and includes a transcutaneous connector including an external portion that provides at least one signal communication port for transport of signals between one or more electrodes and an external device. The neural access device comprises a sensor, an electrical conduit and a connector assembly. The sensor includes a plurality of electrodes that allow chronic access to various living cells of the patient. The electrical conduit comprises a plurality of conductors, and each conductor is electrically connected to one or more electrodes. The connector assembly includes a first portion configured to be placed above the surface of the skin of the patient, a second portion configured to be placed beneath the surface of the skin of the patient, attachment means for securing said second portion under the surface of the skin of the patient, and the at least one signal communication port. The electrical conduit of the neural access device can be detached from the sensor, simplifying the surgical implantation procedure.

In another preferred embodiment, a neural access device with a flexible transcutaneous connector is disclosed. The neural access device is implanted in a patient, and includes a transcutaneous connector including an external portion that provides at least one signal communication port for transport of signals between one or more electrodes and an external device. The neural access device comprises a sensor, an electrical conduit and a connector assembly. The sensor includes a plurality of electrodes that allow chronic access to various living cells of the patient. The electrical conduit comprises a plurality of conductors, and each conductor is electrically connected to one or more electrodes. The connector assembly includes a first portion configured to be placed above the surface of the skin of the patient, a second portion configured to be placed beneath the surface of the skin of the patient, attachment means for securing said second portion under the surface of the skin of the patient, and the at least one signal communication port. The connector assembly of the neural access device includes a flexible sheath which exits through the skin of the patient when the neural access device is implanted in the patient.

In another preferred embodiment, a neural access device with an integrated wireless transmitter or receiver is disclosed. The neural access device is implanted in a patient, and includes a processing module which wirelessly transmits or receives information to or from an external device. The neural access device comprises a sensor, the processing module and a transcutaneous assembly. The sensor includes a plurality of electrodes that allow chronic access to various living cells of the patient. The processing module communicates with the electrodes. The transcutaneous assembly includes a first portion configured to be placed above the surface of the skin of the patient, a second portion configured to be placed beneath the surface of the skin of the patient, and attachment means for securing the second portion under the skin of the patient. According to another aspect of the invention, after the neural access device is implanted, all or part of the processing module can be accessed externally, such as to repair or replace the module, without surgical incision of the skin.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate various embodiments of the present invention, and, together with the description, serve to explain the principles of the invention.

DESCRIPTION OF THE EMBODIMENTS

Figure 1:
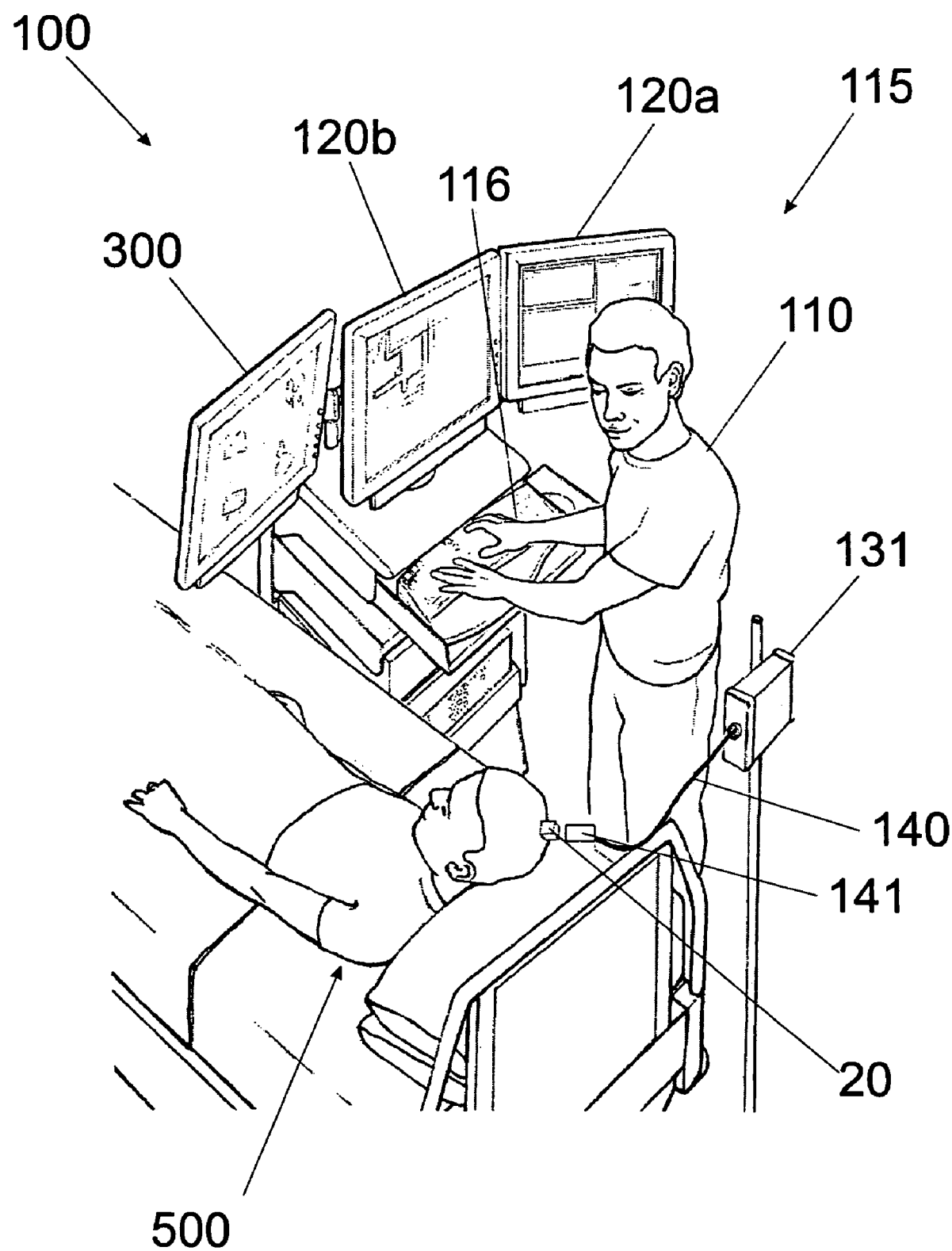
FIG. 1 illustrates a neural interface system consistent with the present invention.

Reference will now be made in detail to the present embodiments of the invention, examples of which are illustrated in the accompanying drawings. Wherever possible, the same reference numbers will be used throughout the drawings to refer to the same or like parts.

Devices, systems and methods consistent with the present invention provide access to living cells of a patient, for the purposes of monitoring cellular electrical activity and/or providing electrical signals to the cells. A neural access device is disclosed, which includes a sensor comprising a plurality of electrodes, each electrode providing long term, or chronic access to the cells. An electrical conduit includes a plurality of conductors, and each conductor is electrically connected to one or more electrodes. The neural access device further includes a connector assembly which can be connected, external to the body of a patient, to a mating receptacle which is used to transport signals to or from one or more other devices external to the body of the patient. The connector assembly includes a first portion which is external to the patient, above the surface of the skin of the patient, transcutaneously and continuously transitioning to a second portion configured to be placed beneath the surface of the skin of the patient. The connector assembly also includes at least one signal communication port, which can be constructed in one or more numerous forms, each form providing one or two way transmission of signals, or signal transport, to or from one or more of the electrodes. Signal transport includes but is not limited to: transmission of cellular activity that is detected from one or more electrodes, transmission of electrical signals to one or more electrodes, combination of transmission of signals detected from one or more electrodes and transmission of signals to one or more electrodes. Potential electrode configurations include having a full set or subset of electrodes that detect cellular activity only, having a full set or subset of electrodes that receive signals from a stimulating device only, and having a full set or subset of electrodes that both detect cellular activity and receive signals from a stimulating device.

In a preferred embodiment, the neural access device is part of a neural interface system, the access device used to at least detect neural signals generated within a patient's body. The detected signals are further processed using various signal processing techniques, and the neural interface system generates processed signals for transmission to a device to be controlled and/or for transmission to a diagnostic or therapeutic device implanted in or external to the patient. In one exemplary embodiment, a neural interface system includes multiple discrete components which can each transmit electronic information to a separate component through the use of a physical cable, including one or more of electrically conductive wires or optical fibers. Alternatively or additionally, transmission of data or other electronic information between discrete components can be accomplished wirelessly, by one or more discrete components including a transceiver that may transmit and receive data such as through the use of "Bluetooth" technology or according to any other type of wireless communication means, method, protocol or standard, including, for example, code division multiple access (CDMA), wireless application protocol (WAP), infrared or other optical telemetry, radiofrequency, microwave or other electromagnetic telemetry, acoustic or ultrasonic telemetry or other telemetric technology.

The neural interface system of the disclosed invention includes a neural access device including a sensor comprising a plurality of electrodes to allow for chronic access of cells, an electrical conduit comprising a plurality of conductors that connect to one or more electrodes and a connector assembly which transcutaneously exits the skin of a patient and includes at least one signal communication port that provides signal transport to or from one or more electrodes. The neural interface system also includes a processing unit that receives these multicellular signals from the neural access device, and utilizes various signal processing, electronic, mathematic, neural net and other techniques and processes to produce a processed signal used to control a device such as a prosthetic limb, ambulation vehicle, communication device, robot, computer, electrical stimulation device or other controllable device. The system includes two or more discrete components, such as those defined by a housing or other enclosing or partially enclosing structure, or those defined as being detached or detachable from another discrete component.

Any and all discrete components may be internal to the body of the patient, external to the body of the patient, as well as implanted in the patient but transcutaneously protruding through the skin such as to be accessible for connection to a physical cable. Discrete components can include, in whole or in part, numerous functions and/or components of a neural interface system or components to be used in combination with the neural interface system. Examples of discrete components include but are not limited to: a neural access device, a multicellular sensor, a signal processing unit, a controlled device, a display monitor, a calibration or system configuration module, a memory storage device, a telemetry device, a physical cable connecting device, a power supply module, a recharging module, an information recall and display unit, and a system diagnostic unit. In the instance where a discrete component includes a configuration module, the configuration module may include configuration programs, settings and patient or system specific data for multiple patients and/or multiple systems. In those instances, all data for a specific single system is associated, or electronically linked, with that system's unique electronic identifier. The configuration module uses an embedded unique electronic identifier of the system during the configuration process to assure that the proper data is utilized.

The neural access device of the present invention provides chronic access to the cells of a patient utilizing at least one implanted sensor containing multiple electrodes, and a transcutaneous connector which includes a connecting portion which is external to the patient. There are numerous types of cells applicable to the access provided by the present invention including but not limited to: nerve cells, brain cells including motor cortex cells, muscle cells, organ cells, tumor cells and other living cells. In a preferred embodiment, the neural access device further includes electrostatic discharge (ESD) protection means, functioning to prevent undesired electrical energy from reaching the implanted electrodes as a result of an electrostatic discharge imparted on an exposed or other portion of the neural access device. The neural access device may include other integrated functions or improved design features including: a recessed attachment mechanism enabling a low-profile design, a detachable electrical conduit, a flexible transcutaneous portion, embedded identification means, integrated power supplying means, and an electronic function module, such as a signal processing module or a wireless transceiver, which may be replaceable without additional surgery.

Referring now to FIG. 1, a specific use of a neural access device of the present invention is shown. The neural access device of FIG. 1 is incorporated into a brain-machine interface, such as neural interface system 100, comprising implanted components and components external to the body of a patient 500. Other functional systems could make use of the neural access device of the present invention, including but not limited to: an epilepsy monitoring and/or stimulation system, a pain monitoring and/or stimulation system, an obesity monitoring and/or stimulation system, an auditory restoration system, a visual restoration system, a closed loop drug delivery system, other neurological therapy systems and multiple-therapy systems. Patient 500 may include multiple implants including but not limited to: muscle control or stimulation implants, an implantable pump, implantable stimulators and brain or cardiac pacemakers.

The neural access device of FIG. 1 includes a sensor for detecting multicellular signals of the patient. The sensor (not shown), such as a three dimensional array of multiple projections with one or more electrodes along the shaft of each projection, may be implanted in the brain of patient 500, in an area such as the motor cortex. In a preferred embodiment, the sensor is placed in an area to record multicellular signals that are under voluntary control of the patient. Alternatively or in addition to the three dimensional array, the sensor may include one or more wires or wire bundles which include a plurality of electrodes, or other electrode configurations described herebelow. Patient 500 of FIG. 1 is shown as a human being, but other mammals and life forms which produce recordable multicellular signals, or to whom chronic access to or from living cells is desirable, would also be applicable. Patient 500 may be a patient with a spinal cord injury or afflicted with a neurological disease that has resulted in a loss of voluntary control of various muscles within the patient's body. Alternatively or additionally, patient 500 may have lost a limb, and system 100 will include a prosthetic limb as its controlled device.

The various electrodes of the sensor detect multicellular signals, such as neuron spikes, which emanate from the individual neurons of the brain. The sensor, which can comprise one or more discrete components, can be placed at one or more various locations within the body of patient 500, such as at an extracranial site, and preferably in a location to collect multi-cellular signals directly from the central nervous system. The electrodes can take on various shapes and forms, including the penetrating electrodes described hereabove, as well as atraumatic or blunt shapes such as those included in cuff electrodes, subdural grid electrodes and scalp electrodes. The sensor can be placed on or above the surface of the brain without penetrating, such as to detect local field potential (LFP) signals, or on the scalp to detect electroencephalogram (EEG) signals.

The sensor electrodes of system 100 can be used to detect various multicellular signals including neuron spikes, electrocorticogram signals (ECoG), local field potential (LFP) signals, electroencephalogram (EEG) signals and other multicellular signals. The electrodes can detect multicellular signals from clusters of neurons and provide signals midway between single neuron and EEG recordings. Each electrode is capable of recording a combination of signals, including a plurality of neuron spikes. In other uses of the neural access device of the present invention, the sensor electrodes can be used to additionally or alternatively stimulate or otherwise provide electrical signals to the living cells of a patient. In the multi-electrode configuration described herein, specific electrodes may be designated for recording and a different set of electrodes designated for stimulating or otherwise providing electrical signals to the cells. In another preferred embodiment, certain electrodes can be designated to both record and stimulate. Recording electrodes may have different geometries and/or materials of construction than stimulating electrodes, and electrodes intended for both recording and stimulating may have different geometries and/or materials of construction than either recording only or stimulating only electrodes.

A signal processing unit 131 attaches to the neural access device at attachment port 20 which provides chronic access to cells, including the multicellular signals produced by cells of the central nervous system. Attachment port 20 utilizes attachment means to connect to mating connector 141 which transmits or transports signals to processing unit 131 via cable 140. Cable 140 may include electrically conductive wires, optical fibers, other means of transmitting data and/or power, and any combination of those. Mating connector 141 receives or sends signals from or to attachment port 20 via one or more forms of signal connection means described in detail herebelow in reference to the subsequent figures. Either or both mating connector 141 and attachment port 20 may include additional signal processing circuitry such as amplification, filtering, signal selection, and/or multiplexing.

In a preferred embodiment, processing unit 131 receives multicellular signals from the neural access device including the sensor and attachment port 20 and performs various signal processing functions including but not limited to amplification, filtering, sorting, conditioning, translating, interpreting, encoding, decoding, combining, extracting, mathematically transforming, and/or otherwise processing those signals to generate a control signal for transmission to a controlled device. Processing unit 131 may process signals that comprise neuron spikes that are first separated using one or more spike discrimination methods known to those of skill in the art. Processing unit 131 may comprise a single component, as shown in FIG. 1, or multiple components.

In the brain-machine interface of FIG. 1, controlled device 300 is a computer system including a computer display with cursor control, and patient 500 may be controlling one or more of a mouse, keyboard, cursor, joystick, other computer input device, or combinations and/or multiples of these devices. Numerous other controlled devices can be included in system 100, individually or in combination, including but not limited to prosthetic limbs, functional electrical stimulation (FES) devices and systems, robots and robotic components, teleoperated devices, computer controlled devices, communication devices, environmental control devices, vehicles such as wheelchairs, remote control devices, electrical stimulation devices, medical therapeutic and diagnostic equipment such as drug delivery apparatus, and other controllable devices applicable to patients with some form of paralysis or diminished function as well as any device that may be better utilized under direct brain or thought control.

The sensor is connected via an electrical conduit (not shown), preferably a multi-conductor cable, to attachment port 20. Attachment port 20 includes a transcutaneous pedestal which is mounted to the patient's skull and preferably includes multiple conductive pads for connecting to mating connector 141. The electrical conduit includes a separate conductor for each electrode, and may include additional conductors to serve other purposes. In an alternative embodiment, one or more conductors may be connected to multiple electrodes. Various descriptions of the sensor and electrical conduit are described in detail in relation to subsequent figures included herebelow.

The neural access device, including the sensor, electrical conduit, and attachment port 20, may include a unique electronic identifier, such as a unique serial number or any alphanumeric or other retrievable, identifiable code associated uniquely with the system 100 or any implant of patient 500. The unique electronic identifier may take many different forms, such as: a piece of electronic information stored in a memory module; a semiconductor element or chip that can be read electronically via serial, parallel, or telemetric communication; pins or other conductive parts that can be shorted or otherwise connected to each other or to a controlled impedance, voltage, or ground, to create a unique code; pins or other parts that can be masked to create a binary or serial code; combinations of different impedances used to create a serial code that can be read off contacts; features that can be optically scanned and read by patterns and/or colors; mechanical patterns that can be read by mechanical or electrical detection means or by mechanical fit, radio frequency ID, or other frequency spectral codes sensed by radiofrequency or electromagnetic fields; pads or other marking features that may be masked to be included or excluded to represent a serial code; or any other digital or analog coding schemes that can be retrieved from any discrete component.

The discrete component may require power, provided internally or externally, to allow the unique electronic identifier to be retrievable, or no power may be required. Power can be supplied with numerous different forms of energy including but not limited to one or more of: acoustic energy, light energy, electromagnetic energy, electrical energy, mechanical energy, and chemical energy. The unique electronic identifier can be transmitted with many different types of signals including but not limited to: acoustic signals, infrared signals, radiofrequency signals, microwave signals, optical signals and electrical signals.

The unique electronic identifier can be embedded in one or more of the discrete components at the time of manufacture, or at a later date such as at the time of any clinical procedure involving the system, such as a surgery to implant the sensor electrodes into the brain of patient 500. Alternatively, the unique electronic identifier may be embedded in one or more of the discrete components at an even later date such as during system configuration or calibration.

Referring again to FIG. 1, attachment port 20 provides transport of signals to processing unit 131 via cable 140 and mating connector 141. Cable 140, as well as other physical cables incorporated into system 100, may include electrical wires, optical fibers, other means of transmitting data and/or power and any combination of those. The number of individual conductors of cable 140 can be greatly reduced from the number of electrodes of the sensor of the neural access device through signal combination or signal multiplexing circuitry embedded in the neural interface system, such as in the sensor or in attachment port 20, and/or in mating connector 141. Cable 140, as well as all other physical cables incorporated into system 100, may include shielding elements to prevent or otherwise reduce the amount of electromagnetic noise added to the various neural signals, processed neural signals and other signals carried by those cables. In an alternative preferred embodiment, cable 140 is replaced with a wireless connection for transmission of information between processing unit 131 and either attachment port 20 or mating connector 141. Any wireless communication means known to those of skill in the art can be utilized to transmit information between any of the components of system 100.

An operator 110, such as a qualified individual, performs a calibration of system 100 at some time during the use of system 100, preferably soon after implantation of the sensor. As depicted in FIG. 1, operator 110 utilizes configuration apparatus 115 which includes first configuration monitor 120a and second configuration monitor 120b, along with configuration keyboard 116 to perform the calibration routine and other configuration tasks such as patient training, algorithm and algorithm parameter selection, and output device setup. The software programs and hardware required to perform the calibration can be included in the processing unit 131 or in a central processing unit incorporated into configuration apparatus 115. Configuration apparatus 115 can include additional input devices, such as a mouse or joystick, not shown. Configuration apparatus 115 can include various elements, functions, and data including but not limited to: memory storage for future recall of calibration activities, operator qualification routines, standard human reference data, standard synthesized reference data, neuron spike discrimination software, operator security and access control, controlled device data, wireless communication means, remote (such as via the internet) calibration communication means and other elements, and functions and data used to provide an effective and efficient calibration on a broad base of applicable patients and a broad base of applicable controlled devices. The unique electronic identifier can be embedded in one or more of the discrete components at the time of system configuration, including the act of identifying a code that was embedded into a particular discrete component at its time of manufacture, and embedding that code in a different discrete component.

Operator 110 may be a clinician, technician, caregiver, or even the patient themselves in some circumstances. Multiple operators may be needed to perform a calibration, and each operator may be limited by system 100, via passwords and other control configurations, to only perform specific functions. For example, only the clinician may be able to change specific critical parameters, or set upper and lower limits on other parameters, while a caregiver, or the patient, may not be able to access those portions of the calibration procedure. The calibration procedure includes the setting of numerous parameters needed by the system 100 to properly control controlled device 300. The parameters include but are not limited to various signal conditioning parameters as well as selection and de-selection of specific subsets of multicellular signals for processing to generate the device control signal. The various signal conditioning parameters include, but are not limited to, threshold levels for amplitude sorting and filtering levels and techniques.

The operator 110 may be required by system 100 to perform certain tasks, not part of the actual calibration, to be qualified and thus allowed to perform the calibration routine. The tasks may include analysis of pre-loaded multicellular signals, either of synthetic or human data, and may include previous data captured from patient 500. The mock analysis can be tested for accuracy, requiring a minimum performance for the calibration routine to continue.

The calibration routine will result in the setting of various calibration output parameters. Calibration output parameters may comprise one or more of: electrode selection, neural signal selection, neuron spike selection, electrocorticogram signal selection, local field potential signal selection, electroencephalogram signal selection, sampling rate by signal, sampling rate by group of signals, amplification by signal, amplification by group of signals, filter parameters by signal, and filter parameters by group of signals. In a preferred embodiment, the calibration output parameters are stored in memory in one or more discrete components, and the parameters are linked to the system unique electronic identifier.

Calibration routines may be performed on a periodic basis, and may include the selection and deselection of specific neural signals over time. The initial calibration routine may include initial values, or starting points, for one or more of the calibration output parameters. Subsequent calibration routines may involve utilizing previous calibration output parameters which have been stored in a memory storage element of system 100. Subsequent calibration routines may be shorter in duration than an initial calibration and may require less patient involvement. Subsequent calibration routine results may be compared to previous calibration results, and system 100 may require a repeat of calibration if certain comparative performance is not achieved.

In the performance of the calibration routine, the operator 110 may involve the patient 500 or perform steps that do not involve the patient 500. The operator 110 may have patient 500 think of an imagined movement, imagined state, or other imagined event, such as a memory, an emotion, the thought of being hot or cold, or other imagined event not necessarily associated with movement. The patient participation may include the use of one or more cues such as audio cues, visual cues, olfactory cues, and tactile cues. The patient 500 may be asked to imagine multiple movements, and the output parameters selected during each movement may be compared to determine an optimal set of output parameters. The imagined movements may include the movement of a part of the body, such as a limb, arm, wrist, finger, shoulder, neck, leg, ankle, and toe, as well as imagining moving to a location, moving at a velocity, or moving at an acceleration.

Other calibration input parameters include various properties associated with the multicellular signals including one or more of: signal to noise ratio, frequency of signal, amplitude of signal, neuron firing rate, average neuron firing rate, standard deviation in neuron firing rate, modulation of neuron firing rate as well as a mathematical analysis of any signal property including modulation of any signal property. Additional calibration input parameters may include but are not limited to: system performance criteria, controlled device electrical time constants, controlled device mechanical time constants, other controlled device criteria, types of electrodes, number of electrodes, patient activity during calibration, target number of signals required, patient disease state, patient condition, patient age, and other patient parameters and event based (such as a patient imagined movement event) variations in signal properties including neuron firing rate activity. In a preferred embodiment, one or more calibration input parameters are stored in memory and linked to the embedded, specific, unique electronic identifier.

It may be desirous for the calibration routine to exclude one or more multicellular signals based on a desire to avoid signals that respond to certain patient active functions, such as non-paralyzed functions, or even certain imagined states. The calibration routine may include having the patient imagine a particular movement or state, and based on sufficient signal activity such as firing rate or modulation of firing rate, exclude that signal from the signal processing based on that particular undesired imagined movement or imagined state. Alternatively, real movement accomplished by the patient may also be utilized to exclude certain multicellular signals emanating from specific electrodes of the sensor.

Figure 2A:
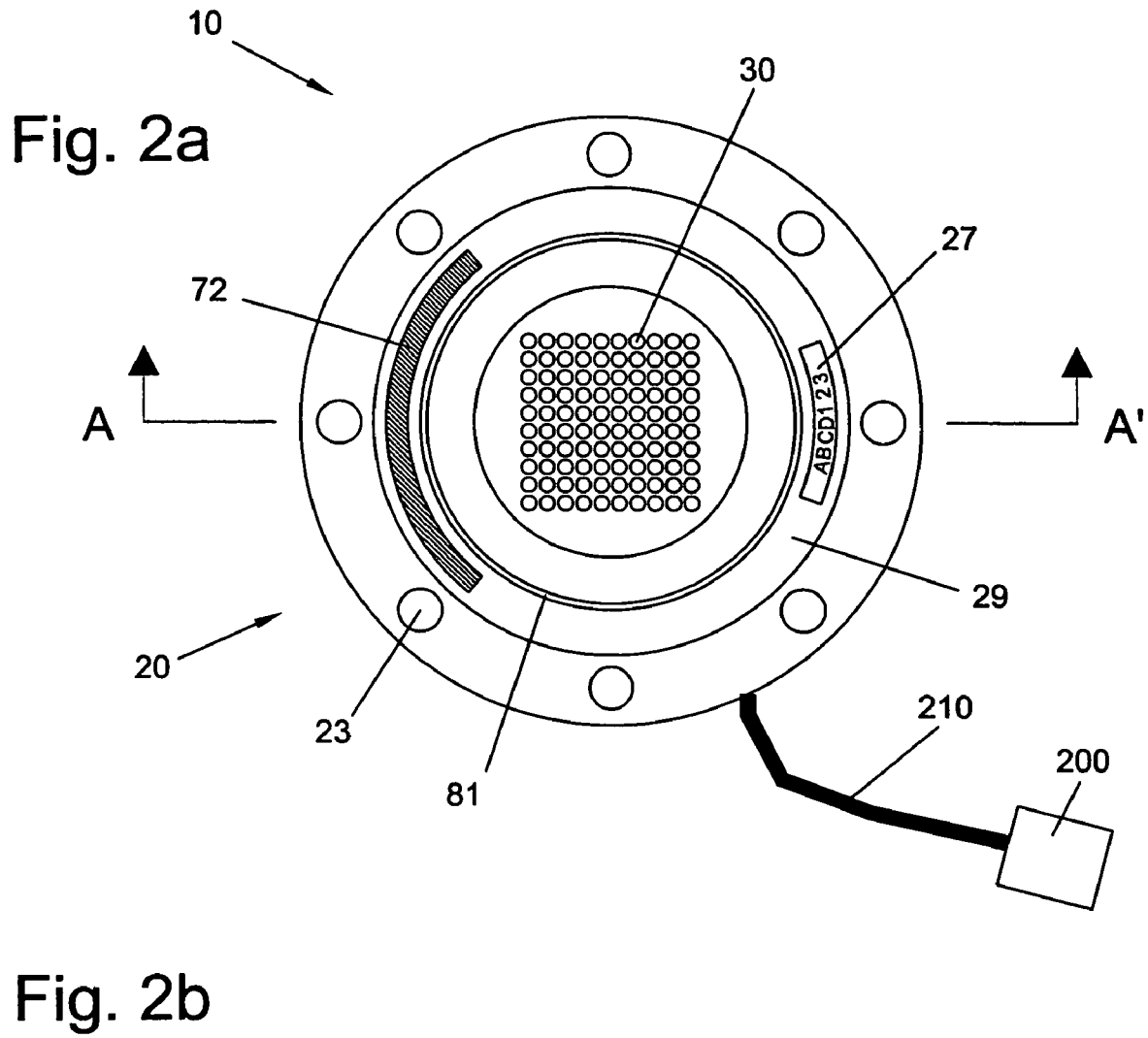
FIG. 2a illustrates a top view of a neural access device consistent with the present invention.
Figure 2B:
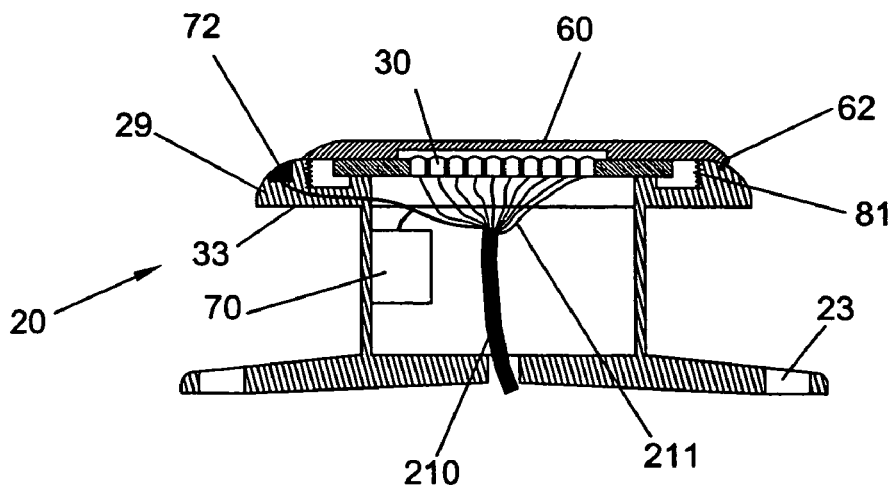
FIG. 2b illustrates a cross-sectional side view of the neural access device of FIG. 2a at section A-A' with a protective cap attached.

Referring now to FIGS. 2a and 2b, a neural access device consistent with an embodiment of the present invention is illustrated. Neural access device 10 includes sensor 200, which includes one or more discrete components (only one shown). Neural access device 10 also comprises a plurality of electrodes (not shown) that, when device 10 is surgically implanted, provide chronic access to the living cells of a patient. Long term or chronic access to living cells, such as neurons of the central nervous system, can be utilized in various diagnostic, therapeutic and other systems. Access that includes detection, or recording of multi-cellular electrical activity, such as the recording of neuron spikes, can be utilized by a brain-machine interface, a neurological disorder monitoring system such as an epilepsy monitor, a closed loop drug delivery system based on neurological signals, and other applications whose output signal is based, in whole or in part, on cellular electrical activity. Access that includes stimulation or otherwise providing electrical signals directly to or around living cells, can be utilized by pain control devices, neurological treatment devices such as stimulators treating epilepsy or Parkinson's Disease, alert devices, visual stimulators, auditory stimulators, and other therapeutic and diagnostic applications. Access can also include both recording and stimulating, using the same or different groups of electrodes, and can be utilized by numerous types of devices including but not limited to closed loop epilepsy treatment devices and brain-machine interface devices.

Sensor 200 is attached via an electrical conduit, such as wire bundle 210, to a connector assembly, such as attachment port 20. Wire bundle 210 is preferably a multi-conductor cable, including multiple wires, conductors 211 surrounded by a flexible jacket, with each conductor surrounded by an insulating material. In a preferred embodiment, a minimum of one conductor is attached to each electrode of sensor 200. Alternatively, signal conversion or signal multiplexing means are provided in sensor 200 such that a reduced number of conductors can be included in the electrical conduit, and/or a fiber optic cable can be used to transfer signals between sensor 200 and attachment port 20. In another alternative embodiment, a signal conductor 211 of wire bundle 210 may be attached to multiple electrodes, reducing the number of total conductors 211 included in wire bundle 210.

Flange 29, located in the upper portion of attachment port 20, includes a bottom surface, skin contacting portion 33, that makes contact with the surface of the patient's skin when device 10 is implanted. The portion of attachment port 20 located above skin contacting portion 33 remains above the surface of the skin of the patient, and the portion of attachment port 20 located below skin contacting portion 33 remains below the surface of the skin of the patient. The base of attachment port 20 includes attachment means, such as screw holes 23, for securing the portion of attachment port 20 below skin contacting portion 33 to a structure, such as bone, under the skin of the patient. For intra-cranial placement of sensor 200, attachment port 20 may be attached on top of the skull of the patient utilizing surgical bone screws placed through screw holes 23 and into the skull. Alternatively or additionally, suture, surgical staples, or other fixation means can be passed through screw holes 23 to an internal structure such as fascia or other tissue.

Attachment port 20 may include rigid as well as more flexible portions. Attachment port 20 may be constructed of a rigid biocompatible metal such as titanium or stainless steel, or may be constructed of or include, at least in part, flexible biocompatible materials such as a silicone elastomer. Flexible materials may be advantageous at and near the portion of attachment port 20 that surrounds the skin exit site when neural access device 10 is implanted in the patient. It may be desirous for a majority of the external portion, or even the entire external portion, of attachment port 20 to be constructed of flexible materials for both patient comfort and safety issues.

Figure 3:
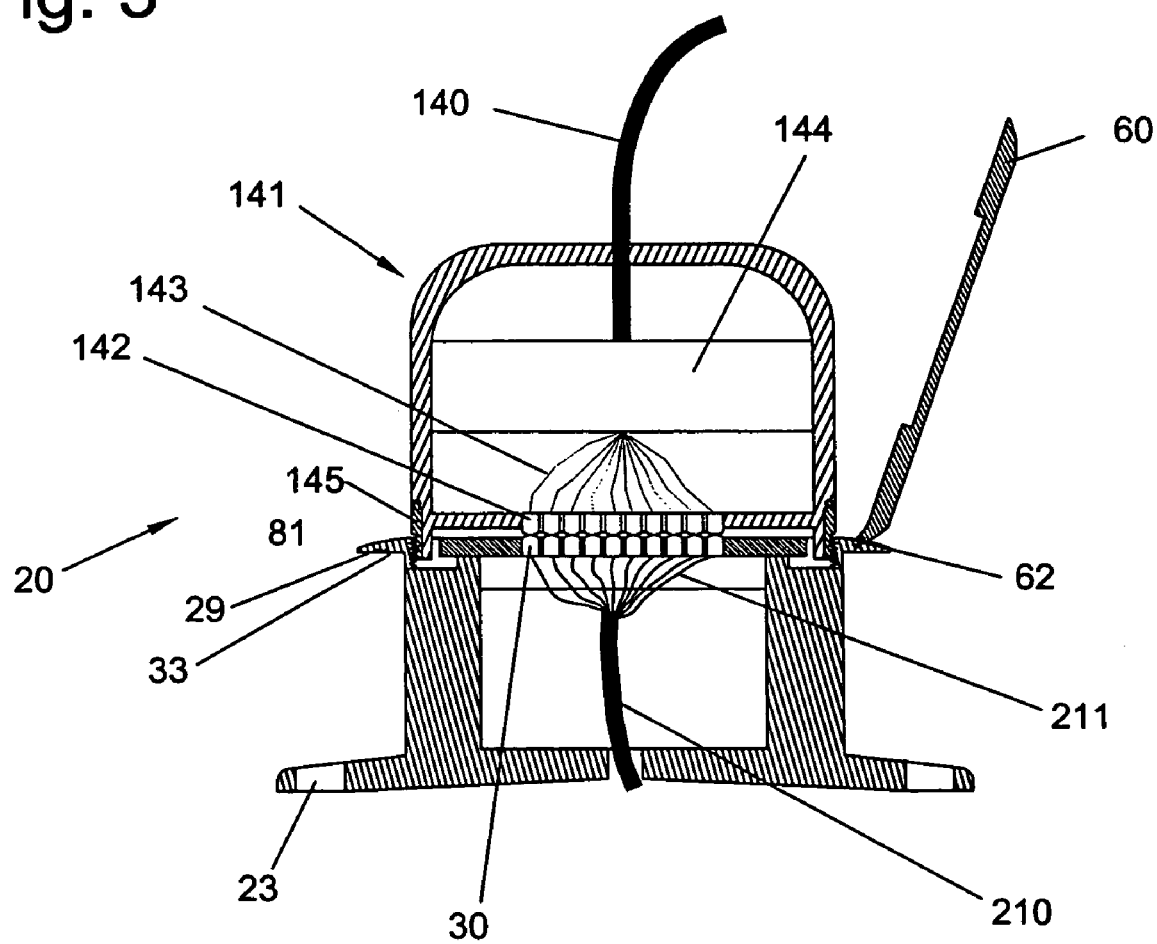
FIG. 3 illustrates a cross-sectional side view of another exemplary embodiment of a neural access device consistent with the present invention.

Attachment port 20 includes engagement means, such as internal threads 81, which are used to connect with a mating connector, not shown, and described in detail in reference to FIG. 3 herebelow. In embodiments in which a majority of the external portion of attachment port 20 is constructed of a flexible material such as silicone, the engagement means, such as internal threads 81, may be made of a rigid material, such as a metal or rigid plastic, which is embedded in the silicone elastomer. Internal threads 81 are located close to the plane of skin contacting surface 33, and in an alternative, preferred embodiment, internal threads 81 extend through or are located entirely below the plane of skin contacting surface 33 such that the portion of attachment port 20 which resides above skin contacting surface 33 is very short or low-profile. This minimally exposed external portion provides numerous advantages relating to safety and aesthetics. For example, a long external portion would allow large torque to be created, producing undesired force, especially on the attachment means such as bone screws placed through screw holes 23 and into the skull of the patient. Various forms of engagement means can be employed, including but not limited to magnetic connections, frictional engagement, bayonet locking mechanisms, mechanical latches, and other electromechanical attachment mechanisms including locking connections which require a key or other security item to attach and detach the mating connector.

Neural access device 10 includes at least one signal communication port for providing signal transport to or from one or more of the electrodes. The device 10 of FIGS. 2a and 2b includes a grid of conductive pads 30, wherein each of the included conductive pads 30 mate with a conducting portion of a mating connector, not shown, but described in detail in reference to FIG. 3 herebelow. Conductive pad 30 may include a surface made of gold or other suitable conductive material. In the preferred embodiment, each of the conductive pads connects to a specific electrode via wire bundle 210 which includes multiple conductors 211, such that electrical signals can be received from or sent to the individual electrodes of sensor 200. Additional conductive pads, not connected to electrodes, may be included for numerous purposes including but not limited to: transfer of power in, transfer of power out, access to embedded ID, access to signal processing circuitry such as signal multiplexing circuitry, access to embedded memory, access to an electronic module, and other signal access purposes.

Attachment port 20 of FIGS. 2a and 2b includes an integrated power supply, such as solar cell 72, integrated into the top, exposed surface of attachment port 20. Since solar cell 72 is on an exposed portion of the patient, such as above the skull of the patient, it will be exposed to light for a substantial portion of the life of the implant. The integrated solar cell 72 can be utilized to provide power to any implanted electronics of neural access device 10, or other implants to which neural access device 10 is connected. The supply of power to implant electronics can obviate the need for an implanted battery or other electrical energy storage device, or more practically reduce the size and/or increase the implant life of such an implanted power supply. Solar cell 72 may be placed underneath a portion of the housing of attachment port 20, as long as the covering portion permits enough light to pass through to activate solar cell 72, such as a transparent or translucent material would allow.

In a preferred embodiment, neural interface 10 includes ESD protection means, such as cap 60, depicted in FIG. 2b but not included, for illustration purposes, from the device 10 of FIG. 2a. Cap 60 is attached to flange 29 of attachment port 20 via a spring loaded hinge 62. The spring loading of hinge 62 is biased such that cap 60 covers conductive pads 30 when a mating connector is not attached to attachment port 20. Cap 60 is preferably constructed to create an electrically conductive outer surface which creates an electrical pathway to an electrically conductive surface of attachment port 20. Electrostatic discharge energy which is applied to cap 60 or attachment port 20 is dissipated through attachment port 20 to the body of the patient without reaching any of conductive pads 30 or any of the electrodes of sensor 200. In an alternative embodiment, cap 60 is made of insulating, non-conductive material, also preventing the energy from electrostatic discharge from reaching conductive pads 30. In a preferred embodiment, the patient is electrically connected, such as via a skin electrode, to a ground of the system. In another preferred embodiment, cap 60 includes multiple filaments attached to its top, not shown, the filaments simulating human hair, in an attempt to camouflage the exposed portion of neural access device 10.

Referring to FIG. 2a, attachment port 20 includes an embossed or engraved identifier, such as visual ID 27, which matches or otherwise is traceable to a unique identifier of neural access device 10, the neural interface system to which neural access device 10 is attached, and/or the patient. Visual ID 27 can take various forms of text, numbers, and other symbology, and can be created at the time of manufacture or at a later date. Alternatively or additionally, other forms of unique identifier can be employed, such as an electronically retrievable unique code, retrievable via wired or wireless communication means.

Referring to FIG. 2b, attachment port 20 may include an integrated module, such as electronic module 70, which performs additional functions relating to or separate from the signal transport to or from the electrodes to the signal communication ports of neural access device 10. Module 70 may include a signal processing function such as signal amplification, signal selection, signal deselection, signal multiplexing, and neuron spike sorting. The signal processing function may also include one or more of: setting an amplitude threshold, setting a sampling rate, setting filtering parameters, setting amplification levels, and other signal conditioning techniques. Module 70 may perform a memory storage function, storing one or more of implant unique ID, system configuration or evolution information including adaptive processing information, signal processing information, and calibration information.

Module 70 may perform a supply of power function, the module including one or more of a battery, a capacitor, other energy storage device, and an energy conversion device. The various energy storage devices may be rechargeable, such as via a specific conductive pad. Module 70 may provide power to the sensor electrodes, to a separate implant, and/or to a separate electronics module integrated into the neural access device 10. Module 70 may include a wireless receiver, a wireless transmitter, or a wireless transceiver. Module 70 may include an energy absorption or shunting element, comprising of electronic circuitry known to those of skilled in the art to absorb or shunt high voltage spikes encountered during an ESD event. The energy absorption or shunting element may be coupled to one or more of the conductive pads 30, such that ESD energy received on the pads is absorbed or shunted thus preventing undesired energy from reaching the electrodes of sensor 200. The neural interface device 10 may include multiple ESD protection elements, such as the combination of cap 60 and an electronic module 70 incorporating ESD protection means.

Referring now to FIG. 3, a connector assembly, attachment port 20, includes an array of communication ports, such as conductive pads 30, which provide single or bi-directional transport of signals to the plurality of electrodes of the sensor of the neural access device. An electrical conduit, such as wire bundle 210, connects at a first end to the sensor (not shown) and at a second end to conductive pads 30 via multiple conductors 211. Attachment port 20 includes means for securing a bottom portion of attachment port 20 under the skin of a patient, such as multiple holes 23 through the bottom surface. Bone anchoring screws, such as those used to place attachment port 20 above the skull of the patient, or suture such as that used to place attachment port 20 at a non-bone site, are placed through holes 23 to secure attachment port 20 under the skin of the patient. Near the upper surface of attachment port 20 is a flange 29 spaced an appropriate distance from the bottom surface of attachment 20 such that when attachment port 20 is implanted at its intended location, such as on the top of the skull, the bottom surface of flange 29, skin contacting surface 33, is above, but in contact with, the external surface of the patient's skin. The top surface of flange 29, conductive pads 30, and cap 60 remain above the skin of the patient when the neural access device is implanted in the patient.

Attachment port 20 is shown with mating connector 141 attached. Mating connector 141 includes an array of conductive surfaces, such as mating pads 142, which are aligned and make contact with the array of conductive pads 30 when mating connector 141 is attached to attachment port 20. Means of aligning the two arrays of conductive surfaces, mating pads 142 and conductive pads 30, are included, such as mating thread designs which tighten to a fixed rotational alignment, aligning notches, pegs, recesses, projections and/or cutouts, visual or tactile alignment markers and/or other alignment means. Conductive pads 30 act as the signal communication port. Conductive pads 30 or mating pads 142 may include spring loaded pins to create a secure signal connection with the mating pads. The signal communication ports of the present invention can take on varied forms to perform the function of transport of electrical signals, optical signals, and/or other data or power signals from the neural access device to one or more devices located external to the patient. For optical signal transmission, the signal communication ports may include optical windows, optical lenses, or other optical means of directing light into or out of an optical fiber. The signal communication ports can be configured to receive signals, transmit signals, or both transmit and receive.

Mating pads 142, preferably including a pad for at least each electrode of the neural access device, are individually attached to a signal transport conduit, such as a wire 143. Each of the wires 143 are shown connecting to module 144 which can be used to provide signal processing to the signals, such as recorded signals received from the electrodes. Signal processing can include filtering, amplification, analog to digital conversion, signal multiplexing, electrical to optical signal conversion and/or other signal processing means. In the preferred embodiment, module 144 performs at a minimum electrical to optical signal conversion and is attached to a fiber optic cable 140, carrying bi-directional transport of signals. In an alternative embodiment, cable 140 is a multi-conductor electrical cable or a combination of one or more wires and one or more optical fibers. In another alternative embodiment, module 144 further includes wireless transmission and/or receiving means, obviating the need for cable 140. In this particular embodiment, mating connector 141 or module 144 may further include an integrated power supply, such as a battery or rechargeable battery. Referring still to this wireless configuration of module 144, mating connector 141 may include a port, not shown, to allow electrical connection for power supply or other electrical connection purposes, and mating connector 141 may be designed to have a finite life, being mass produced at low cost such as to allow frequent replacement, thus providing the latest configuration and state of the art technology at all times, and avoiding maintenance and other requirements of long term use medical devices.

Attachment port 20 includes a protective cover, such as cap 60, which is preferably constructed of a conductive material electrically connected to attachment port 20. Cap 60 is normally biased closed, via a spring loaded hinge 62, covering conductive pads 30 and thus reducing the likelihood of ESD energy reaching the electrodes of the neural access device. When an operator, who has accumulated a sufficient amount of electrostatic energy, touches cap 60, the energy is safely released through the cap to the housing and to the large skin surface of the patient, dissipating the charge of the operator and also avoiding the undesired energy reaching the electrodes.

In connecting mating connector 141, the operator rotates cap 60 away from the array of conductive pads 30, aligns mating connector 141 with attachment port 20, via an alignment notch, visual alignment indicator, or other alignment means, and rotates collar 145 of mating connector 141, such that collar 145 mates with internal threads 81 of attachment port 20. The engagement means of attachment port 20, internal threads 81, extend below skin contacting surface 33 of flange 29 thus creating a very short exposed projection of attachment port 20 when implanted, while allowing a sufficiently long engagement of threads. Numerous forms of recessed attachment means, as well as attachment means that avoid large insertion and/or torsional forces, could be utilized, including but not limited to: magnets and magnetic materials incorporated into attachment port 20 and mating connector 141, various thread configurations, internal or external, that extend below the plane of a skin contacting surface, latching mechanisms including push latching mechanisms and latches that further include a releasing lever, bayonet locks and mechanical press fit or frictional engagement mechanisms.

Figure 4A:
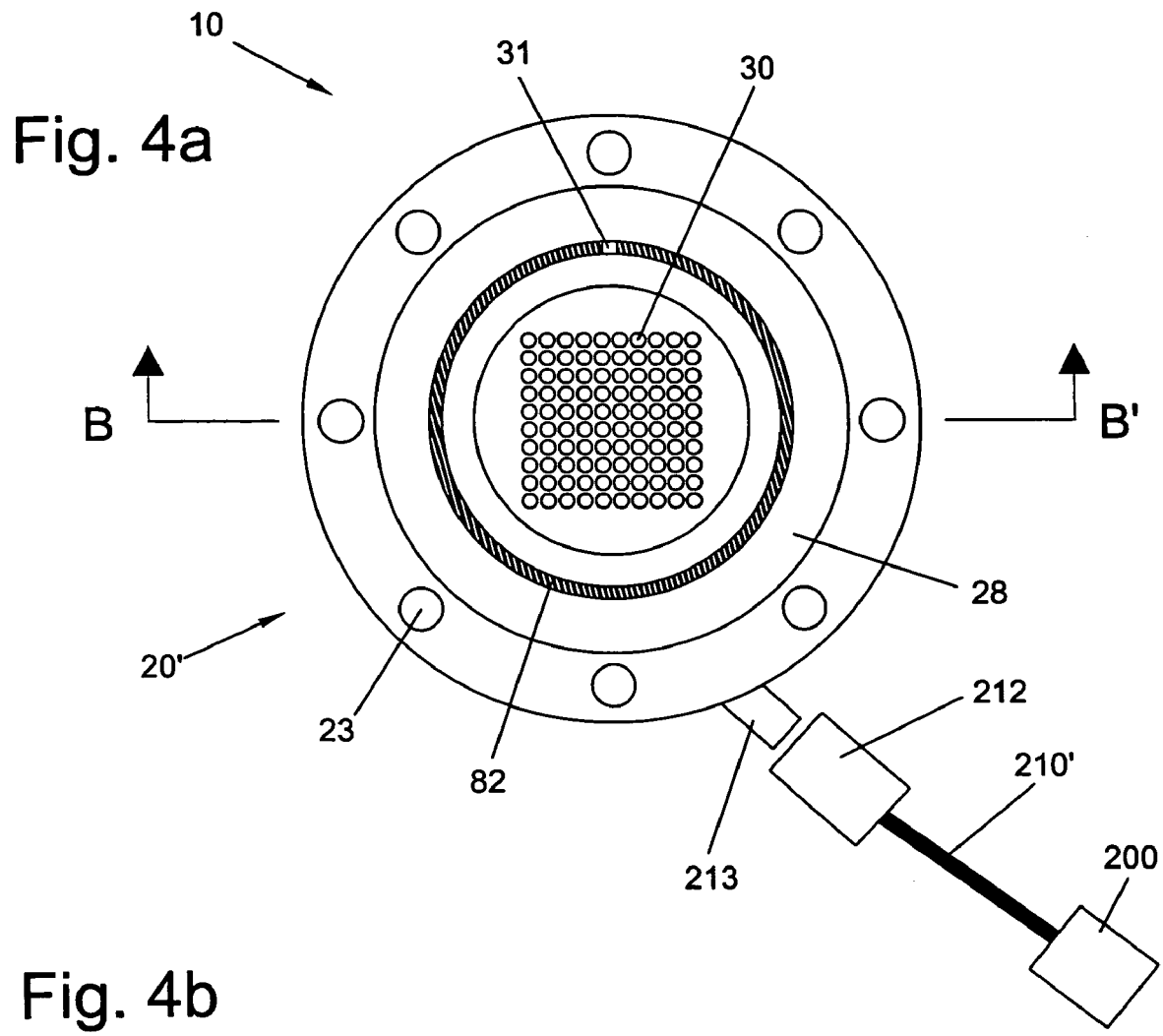
FIG. 4a illustrates a top view of another exemplary embodiment of a neural access device consistent with the present invention.

Referring now to FIG. 4a, neural access device 10 includes a two-piece, attachable design wherein sensor 200, which includes a plurality of electrodes that allow chronic access of the living cells of a patient, is attached to an electrical conduit, wire bundle 210' which includes a plurality of conductors, each conductor attached to one or more electrodes of sensor 200. Wire bundle 210' includes at its other end an attachable connector, such as wire bundle connector 212. Wire bundle connector 212 includes connection means for the individual conductors of wire bundle 210' and mates with a multi-conductor receptacle, wire bundle receptacle 213 of a connector assembly, attachment port 20'. Wire bundle connector 212 can form a secure attachment with wire bundle receptacle 213 utilizing various means including but not limited to: press fit of individual conductor connections such as frictional engagement of multiple male and female pins, press fit connection, threads, bayonet lock or other multiple conductor wire connection means. The attachable design of FIG. 4a allows independent placement of sensor 200, such as in the motor cortex of the brain of the patient, and attachment port 20', such as on the skull of the patient with bone screws placed through holes 23 and into the skull. After both sensor 200 and attachment port 20' are placed, the signal connection can be made by attaching wire bundle connector 212 to wire bundle receptacle 213, thus simplifying the surgical procedure and avoiding unnecessary forces encountered prior to both sensor 200 and attachment port 20' being secured in place.

Attachment port 20' of FIG. 4a further includes means of aligning a mating connector, not shown, such as to properly align the array of conductive pads 30 with the corresponding connections of the mating connector. A recessed portion, such as notch 31 is included at a specific location on external threads 81, wherein notch 31 mates with an appropriately located projection on the mating connector. Numerous forms of mechanical and/or visual alignment means can be incorporated into attachment port 20' and/or its mating connector to properly align the signal communication ports, such as conductive pads 30 of attachment port 20', with the communication pathways of the mating connector to provide signal transport to or from one or more electrodes of the neural access device to a separate device, external to the patient.

Figure 4B:
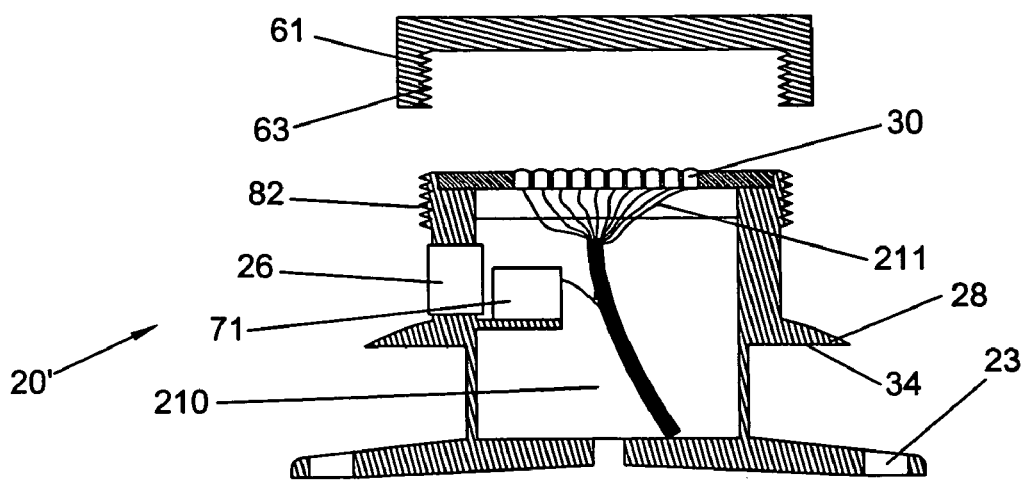
FIG. 4b illustrates a cross-sectional side view of the neural access device of FIG. 4a at section B-B' further depicting a protective cap.

Referring now to FIG. 4b, attachment port 20' includes an annular flange 28, that has a bottom surface comprising skin contacting portion 34, that makes contact with the surface of the patient's skin when device 10 is implanted. The portion of attachment port 20' located above skin contacting portion 34 remains above the surface of the skin of the patient, and the portion of attachment port 20' located below skin contacting portion 34 remains below the surface of the skin of the patient. The base of attachment port 20' includes attachment means, such as screw holes 23, for securing the portion of attachment port 20' below skin contacting portion 34 to a structure, such as bone, under the skin of the patient. For intra-cranial placement of sensor 200, attachment port 20' may be attached on top of the skull of the patient utilizing surgical bone screws placed through screw holes 23 and into the skull. Alternatively or additionally, suture or other fixation means can be passed through screw holes 23 to an internal structure such as the fascia or other tissue.

Attachment port 20' may include rigid as well as more flexible portions. Attachment port may be constructed of a biocompatible metal such as titanium or stainless steel, or may be constructed of or include, at least in part, flexible biocompatible materials such as a silicone elastomer. Flexible materials may be advantageous at and near the portion of attachment port 20 that surrounds the skin exit site when neural access device 10 is implanted in the patient. It may be desirous for a majority of the external portion, or even the entire external portion, of attachment port 20 to be constructed of flexible materials for patient comfort and safety issues.

Attachment port 20' includes engagement means, such as external threads 82, which are used to connect with a mating connector, not shown, and a protective cap, such as removable cap 61 which includes internal cap threads 63 that mate with external threads 82 of attachment port 20'. Removable cap 61 can provide numerous functions in addition to protecting the top surface of attachment port 20' from damage. Removable cap 61 can help prevent electrostatic discharge energy from reaching the electrodes of the neural access device. Removable cap 61 may be constructed of insulating material to isolate the electrodes, or be made conductive such that electrostatic discharge energy is dissipated from an operator through the cap, to the conductive surface of attachment port 20' and eventually to the skin of the patient to which the surface of attachment port 20' makes contact. Removable cap 60 may include means of permanent connection to attachment port 20' such as a conductive strap, not shown. In an alternative embodiment, removable cap 61 may include thru holes from the top to bottom surface such that when the removable cap 61 is properly positioned, the thru holes are aligned with the conductive pads 30, allowing a mating connector to be attached with removable cap 61 in place. When removable cap 61 is rotated, the thru holes are intentionally out of alignment with the conductive pads 30, protecting the conductive pads from damage, contamination and ESD. Engagement means between cap 61 and a mating connector, not shown, would be provided.

Attachment port 20' includes an array of communication ports, such as conductive pads 30, which provide single or bi-directional transport of signals to the plurality of electrodes of the sensor of the neural access device. Electrical conductors 211 are attached to the conductive pads 30 and collectively are incorporated into internal wire bundle 214. Internal wire bundle 214 connects to wire bundle receptacle 213 depicted in FIG. 4a, which in turn can be connected, such as during implantation surgery, to wire bundle connector 212 and thus the electrodes of sensor 200 via wire bundle 210.

Attachment port 20' of FIG. 4b further includes an internal power source, such as battery 71, which includes an electrical conductor incorporated into internal wire bundle 214. Power from battery 71 can be supplied to a separate electronic component of attachment port 20', not shown, or to signal processing, multiplexing, electrical to optical signal conversion means, or other electronics incorporated into sensor 200, also not shown. Incorporated into a portion of attachment port 20' above skin contacting surface 34 is an access door 26, which when opened or removed, provides access to battery 71, allowing replacement of the battery or otherwise providing access to an internal component of attachment port 20'.

Figure 5:
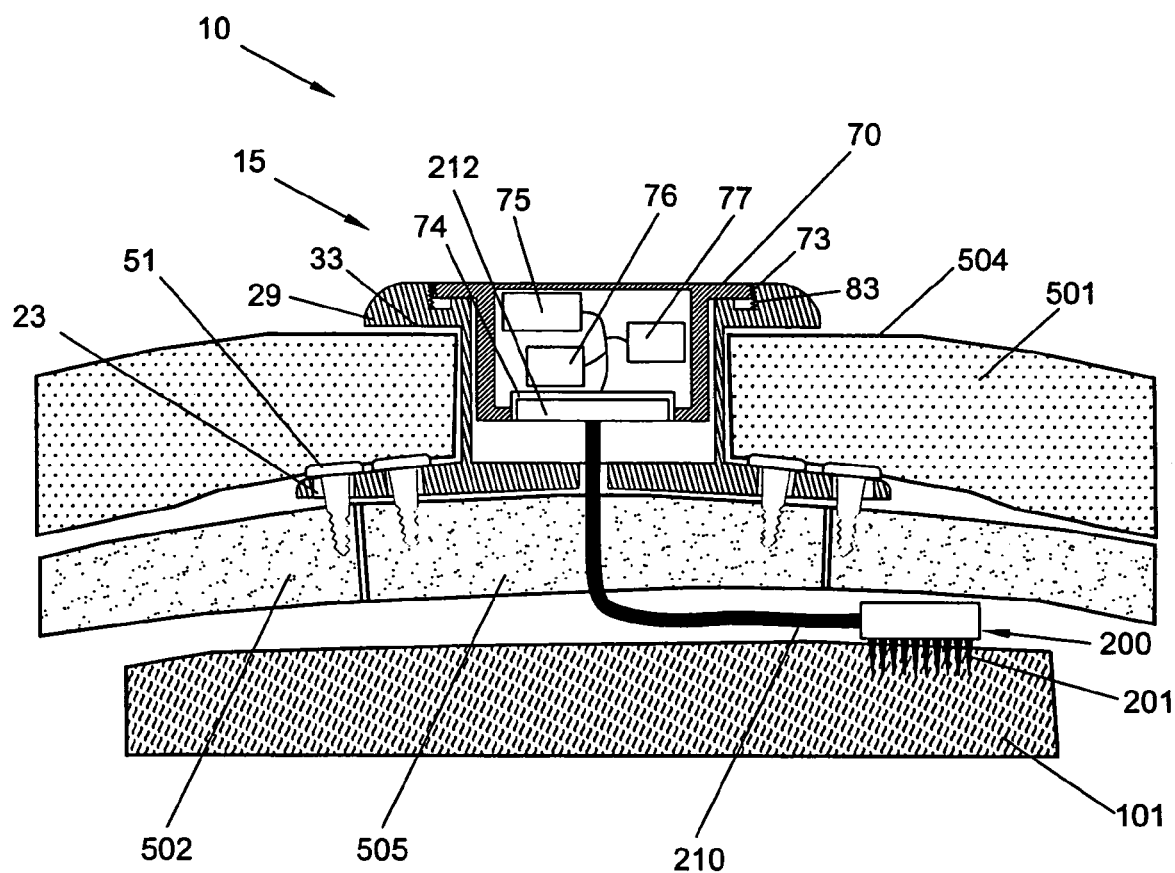
FIG. 5 illustrates a cross-sectional side view of another exemplary embodiment of a neural access device consistent with the present invention.

Referring now to FIG. 5, the neural access device includes sensor 200, comprising a plurality of electrodes 201, that allow chronic access to the living cells of a patient. The electrodes 201 of sensor 200 are placed through an opening in the skull 502 and into the brain 101 of the patient, such as in the cerebral cortex. While FIG. 5 shows sensor 200 inserted into the cerebral cortex, sensor 200 may be placed in any location of a patient's brain allowing for sensor 200 to either detect electrical brain signals or impulses, or stimulate brain cells. Other locations for sensor 200, such as those outside of the cranium, are also applicable for recording of multicellular signals as well as therapeutic stimulation of cells. Non-penetrating electrode configurations, such as subdural grids, cuff electrodes and scalp electrodes are applicable both inside the cranium (such as to record LFPs), in, on or near peripheral nerves, and on the surface of the scalp (such as to record EEGs). Although FIG. 5 depicts the sensor as a single discrete component, in alternative embodiments the sensor may comprise multiple discrete components. Multiple sensor components can be implanted in the brain, at an extracranial location, or any combination of locations for the multiple discrete components making up the sensor. Each discrete component can have as few as a single electrode, with the cumulative sensor containing a plurality of electrodes. Each electrode is capable of recording a plurality of neurons, or other electrical activity, or for stimulating multiple cells.

While FIG. 5 shows sensor 200 as eight electrodes 201 of similar construction, sensor 200 may include one or more electrodes having a variety of sizes, lengths, shapes, forms, and arrangements. Moreover, sensor 200 may be a linear array (e.g., a row of electrodes) or a three-dimensional array (e.g., a matrix of rows and columns of projections including electrodes). Each electrode 201 extends into brain 101 to detect one or more electrical neural signals generated from the neurons located in proximity to the electrode's placement within the brain. Neurons may generate such signals when, for example, the brain instructs a particular limb to move in a particular way.

In the embodiment shown in FIG. 5, each electrode 201 may be connected to a transcutaneous assembly, such as communication port 15, at a connecting element, such as module connector 74 which mates with wire bundle connector 212 of wire bundle 210. Communication port 15 may be secured to skull 222 by, for example, the use of an adhesive or screws, and may even be placed partially inside the skull if desired. The portion of skull 502 which is removed during the implantation procedure, known as a bone flap, can be replaced near the end of the surgery, or an artificial covering can be used. In FIG. 5, bone flap 505 is secured to communication port 15 via bone screws 51 placed through inner screw holes 23. Securing communication port 15 to the remaining portion of skull 502 via bone screws 51 placed through holes 23 not only secures communication port 15 to the skull but also fills in the craniotomy with the original bone flap now secured to communication port 15. A protective plate may be used in place of the bone flap, or the communication port 15 can have a lower projection, not shown, that fills in the craniotomy. In an alternative embodiment, communication port 15 is secured to the skull away from the craniotomy and the bone flap, or other protective plate is used to fill the craniotomy with use of surgical bridging straps, such as those made of titanium, and bone screws.

After the craniotomy is replaced or covered, the scalp 501 is brought continuously around the perimeter of communication port 15 under the bottom surface of flange 29 at skin contacting surface 33, such that skin surface 504 is in contact with skin contacting surface 33. Suture, not shown, is used to create a relatively tight fit to assist in healing and provide a durable transcutaneous exit of a non-biologic device. Antibacterial and other therapeutic and prophylactic agents are used to prevent infection and promote healing, and in a preferred embodiment are incorporated into the surface of communication port 15. While FIG. 5 depicts placement of sensor 200 into the brain and communication port 15 transcutaneously exiting the scalp and secured to the skull, other locations within the body of a patient will use similar methods of surgical implantation, inserting the electrodes of sensor 200 near living cells, and placing the transcutaneous assembly through the skin while securely attaching an internal portion to one ore more internal structures.

Electrodes 201 receive electrical signals and/or transfer the detected neural signals to communication port 15 via the conductors of wire bundle 210. Each projection of sensor 200 may include a single electrode, such as an electrode at the tip of the projection, or multiple electrodes along the length of each projection. As shown in FIG. 5, wire bundle 210 may pass out of the opening in skull 502 into a bottom opening of communication port 15. Wire bundle 210, such as a multi-conductor cable connecting each electrode to communication port 15, may then run underneath the patient's skin 224 to connect to communication port 15. Persons skilled in the art, however, will appreciate that arrangements other than the one shown in FIG. 5 may be used to connect sensor 200 to communication port 15 via wire bundle 210.

Communication port 15 may preprocess the received neural signals (e.g., impedance matching, noise filtering, or amplifying), digitize them, and further process the neural signals to extract neural information that it may then transmit to an external device (not shown), such as a further processing device and/or any device to be controlled by the processed multicellular signals. For example, the external device may decode the received neural information into control signals for controlling a prosthetic limb or a computer cursor, or the external device may analyze the neural information for a variety of other purposes.

Communication port 15 or any signal processing module of the present invention may also conduct adaptive processing of the received neural signals by changing, over time, one or more parameters of the system to achieve or improve performance. Examples of adaptive processing include, but are not limited to, changing a parameter during a system calibration, changing a method of encoding neural information, changing the type, subset, or amount of neural information that is processed, or changing a method of decoding neural information. Changing an encoding method may include changing neuron spike sorting methodology, calculations, thresholds, or pattern recognition. Changing a decoding methodology may include changing variables, coefficients, algorithms, and/or filter selections. Other examples of adaptive processing may include changing over time the type or combination of types of signals processed, such as EEG, LFP, neural spikes, or other signal types. Adaptive processing may be necessary to adapt to death of cells and other changes in neural activity, shifts in electrode position, changes in external device requirements, changes in system performance, and other physiologic and system states that change over time.

The neural access device 10 of FIG. 5 includes an integrated electronic module 70, which can perform multiple functions including but not limited to: signal processing, signal selection, supply of power, memory storage, wireless signal transmission, and wireless signal receipt. Integrated signal processing and signal selection functions reduce the requirements of external devices and standardize the communication protocols with external devices. Such signal processing and signal selections functions include but are not limited to: amplification, filtering, signal selection, signal deselection, signal multiplexing, spike sorting, setting an amplitude threshold, setting a sampling rate, setting filtering parameters, setting amplification levels and other signal processing, signal selection and signal conditioning techniques. Module 70 can include a memory storage function, storing one or more of numerous various pieces of data including but not limited to: implant unique ID, patient information, therapy information, external device information, adaptive processing information, signal processing information and calibration information. Module 70 can include a supply of power function, the module including one or more of a battery, a capacitor, an energy storage device, and an energy converter device. The power supply can be replaceable, such as via replacement of module 70 in entirety, or include an access hatch, or removable door, to replace the power supply. The energy converter device can take various forms including a light to electrical energy converter such as a solar cell, a thermal to electrical energy converter, a vibration or movement to electrical energy converter, or other energy converter. Power can be supplied to various elements of the neural access device 10, including other components of module 70, a separate module of neural access device 10, the electrodes of sensor 200, and even to a separate device including a separate implant of the patient. Module 70 can include a wireless receiver, a wireless transmitter, or both, such that communication to or from an external device can be accomplished without physical wires. Module 70 can be designed to be replaceable, accessible to removal from outside of the patient without surgery.

In the preferred embodiment of FIG. 5, module 70 is removable, such as by rotation of module 70 such that module threads 73 disengage from receiving threads 83 of communication port 15. In another preferred embodiment, module 70 includes power supply 76, such as a battery or a capacitor, which provides power to one or more components of neural access device 10, or a separate device such as a separate implant of the patient. Module 70 may include a electrical connection jack, not shown, such as a jack allowing recharging of the power supply 76 of module 70 while module 70 is in place or after it has been removed from communication port 15. Module 70 may include an access, such as a door, to replace power supply 76. Module 70 may be a mass-produced, single-use device that is replaced on a regular basis. In such a configuration, the power supply would be sealed inside module 70 with no access provided.

Module 70 attaches to the wire bundle 210 at its connector, wire bundle connector 212 via module connector 74, which includes connection points for each conductor of wire bundle 210. Module 70 includes wireless information transceiver, such as wireless assembly 75, which can receive and send information wirelessly to a device external to and/or implanted within the patient. In applications where large amounts of data are to be transmitted, such as in brain-machine interface applications where multi-cellular signals under voluntary control of the patient are used to control a device, multiple wireless transceivers can be incorporated to share in the large amounts of data transfer with differentiating wireless protocols used by each. Module 70 further includes signal processing element 77 which is used to process information received from or to be sent to the electrodes 201 of sensor 200. Signal processing can take various forms as been described in detail throughout this disclosure.

Figure 6:
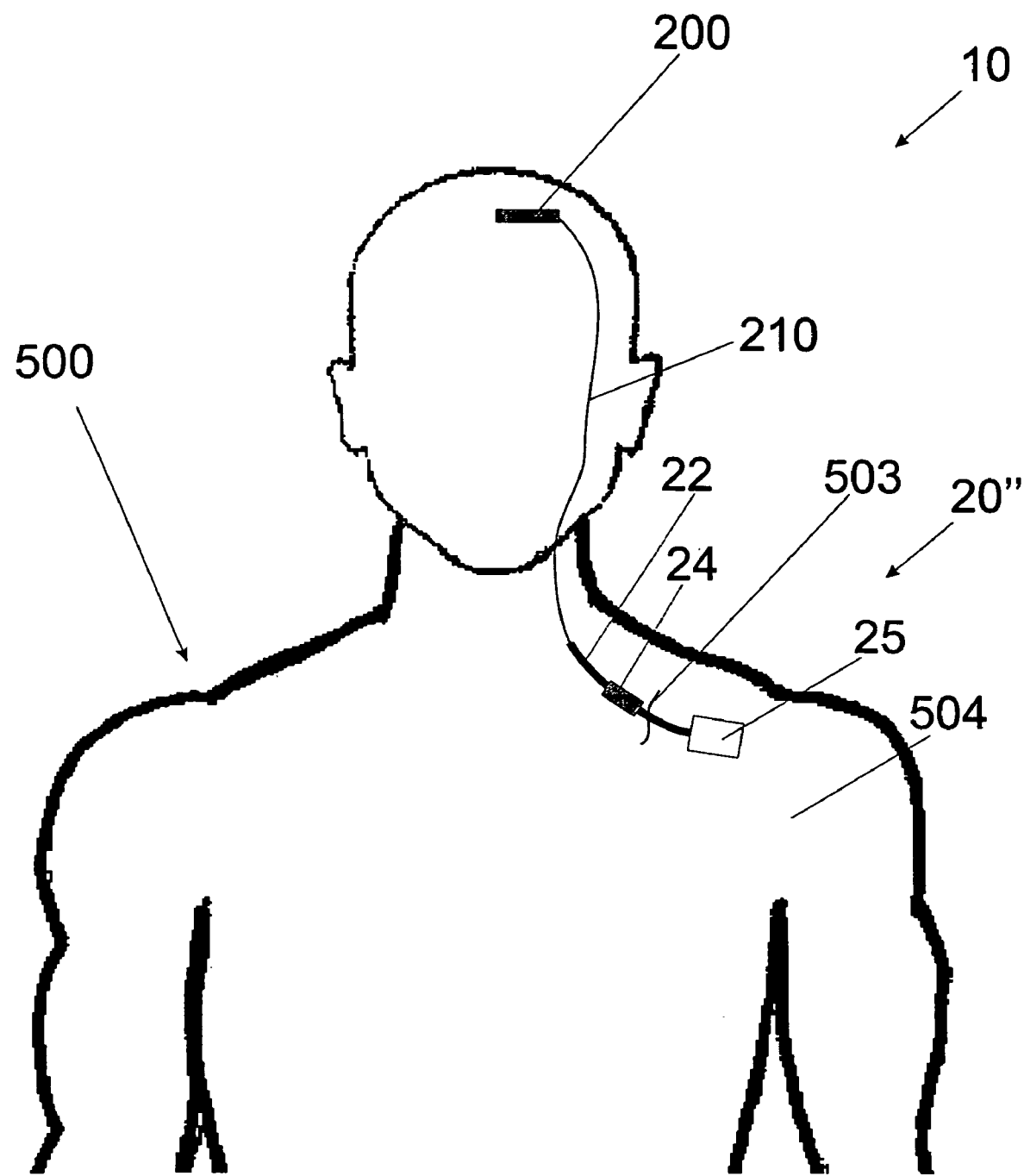
FIG. 6 illustrates another exemplary embodiment of a neural access device consistent with the present invention.

Referring now to FIG. 6, patient 500 may be implanted with another preferred embodiment of neural access device 10 wherein a connector assembly (e.g., attachment port 20") includes a flexible portion, such as flexible housing 22, which exits skin surface 504 of patient 500 at skin exit 503, preferably below the head and shoulders, at an inconspicuous yet accessible location for attachment to an external device. Flexible housing 22 is a flexible tube, including an inner lumen through which multiple conductors can reside, having similar construction and materials to that of transcutaneous catheters used for central venous access and other medical applications. Materials of construction can include flexible forms of silicone, polyurethane, nylon, polyethylene, teflon, polyvinylchloride and other flexible, biocompatible materials. In the implanted portion and near the point intended for transcutaneous exit through the skin, flexible housing 22 includes a woven polyester, or Dacron cuff 24, surrounding its circumference. After implantation, tissue grows into cuff 24 providing the function of securing attachment port 20" to a location beneath the skin of the patient, as well as providing a well known barrier for migration of bacteria and other contamination.

At the implanted end of neural access device 10 is sensor 200, preferably a three dimensional array of multiple projections, one or more projections including one or more electrodes along its shaft, such that electrical signals can be transmitted to or received from various living cells of patient 500. The sensor of FIG. 6 is shown implanted within the cranium of the patient, such as in the motor cortex of the brain. An electrical conduit, comprising a multiple conductor cable, such as wire bundle 210, includes conductors that attach to the electrodes, preferably one conductor for each electrode and each conductor including an insulating jacket, but alternatively groups of electrodes can be electrically attached to single conductors to reduce the diameter of wire bundle 210. Wire bundle 210 exits the cranium to the top of the skull (not shown) under the scalp, and remaining under the skin, travels along the side of the head through the neck to the transcutaneous exit location, skin exit 503. Wire bundle 210 is shown as entering flexible housing 22 near the shoulder area, however flexible housing 22 can be of increased length and cover wire bundle 210 for a longer portion, such as a length closer to sensor 200. In a preferred embodiment, flexible housing 22 is relatively short, as depicted in FIG. 6, protecting wire bundle 210 at locations internal and external, but near to skin exit 503. The wire bundle 210, under flexible housing 22, terminates external to the body at a connector assembly, such as attachment port connector 25, which includes multiple communication ports, such as electrically conductive pads or pins, not shown. A mating connector, also not shown, can be attached to attachment port connector 25 to provide signal transport to or from one or more electrodes, such as to receive multicellular signals or to provide electrical signals to stimulate or otherwise bias multiple cells. One or more components of the neural access device 10 of FIG. 6, such as attachment port connector 25, can include an electronic module, not shown, the module providing one or more of numerous functions including but not limited to: signal processing, signal selection, supply of power, memory storage, wireless signal transmission, and wireless signal receipt.

It should be understood that numerous other configurations of the systems, devices and methods described herein can be employed without departing from the spirit or scope of this application. For example, the neural access device may include a sensor comprised of one or more discrete components. The sensor in total may include a plurality of electrodes that can detect multicellular activity or provide electrical signals to the cells. Electrical wires may be attached to the electrodes and continue to a location external to the body of a patient, or alternatively converted internally to modified electrical signals which can be carried by a reduced number of electrical conductors, by optical fibers, or by a combination of the two. Wireless communication can also be incorporated to eliminate one or more physical cables that otherwise would be implanted in the patient, or attached from the transcutaneous exit site to an external device.

The sensors of the systems of this application can take various forms, including multiple discrete component forms, such as multiple penetrating arrays which can be placed at different locations within the body of a patient as well as combine with electrodes external to the patient. The attachment ports and connector assemblies of this disclosure can also be contained in a single discrete component or multiple discrete components, where multiple components transcutaneously exit the patient at multiple skin penetration locations. The neural access device may include a functional module incorporated into the sensor, the electrical conduit, and/or the attachment port or connector assembly.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A neural access device for implanting in a patient comprising:
   a sensor comprising a plurality of electrodes to allow for chronic access of cells;
   an electrical conduit comprising a plurality of conductors, each conductor electrically connected to one or more of the electrodes;
   a connector assembly comprising:
   a first portion configured to be placed above a surface of a patient's skin;
   a second portion configured to be placed beneath the surface of the patient's skin;

an attachment member for securing the second portion beneath the surface of the patient's skin; and at least one signal communication port configured to transport a signal to and/or from one or more of the electrodes; and an electrostatic discharge protector comprising a removable cap covering the at least one signal communication port and configured to protect the device from electrostatic discharge wherein the signal communication port is configured to transmit cellular activity detected from one or more of the electrodes and electrical signals to one or more of the electrodes wherein the cellular activity is detected from one or more of the electrodes and the electrical signals are transmitted to at least one of the one or more electrodes from which cellular activity is detected.

2. The device of claim 1, wherein the cap comprises an electrically insulating material.

3. The device of claim 1, wherein the cap comprises an electrically conductive material.

4. The device of claim 1, wherein the cap is attached to the connector assembly by a hinge.

5. The device of claim 4, wherein the hinge is spring-loaded.

6. The device of claim 1, wherein the cap comprises at least one filament attached to the cap.

7. The device of claim 6, wherein the at least one filament is designed to resemble human hair.

8. The device of claim 1, wherein the electrostatic discharge protector comprises an integrated circuit element configured to absorb electrical energy to prevent undesired electrical energy from reaching one or more of the electrodes.

9. The device of claim 1, wherein the electrostatic discharge protector comprises at least two redundant elements each configured to prevent undesired electrical energy from reaching one or more of the electrodes.

10. The device of claim 1, wherein the sensor is configured to detect multicellular signals emanating from the central nervous system.

11. The device of claim 10, wherein the multicellular signals comprise one or more of neuron spikes, electrocorticogram signals, local field potential signals, and electroencephalogram signals.

12. The device of claim 1, wherein the sensor is configured to detect multicellular signals from clusters of neurons and provide signals midway between single neuron and electroencephalogram recordings.

13. The device of claim 1, wherein the sensor is configured to transmit electrical signals to the central nervous system.

14. The device of claim 1, wherein the sensor is configured to both transmit and receive electrical signals.

15. The device of claim 1, wherein the patient is a human being.

16. The device of claim 1, wherein the sensor comprises a multi-electrode array.

17. The device of claim 16, wherein the multi-electrode array comprises a plurality of projections extending from a surface, at least one of the plurality of projections comprises at least one electrode along its length.

18. The device of claim 17, wherein the at least one electrode is located near a distal tip of the projection.

19. The device of claim 17, wherein the at least one electrode comprises at least two electrodes along its length.

20. The device of claim 16, wherein electrodes of the multi-electrode array comprise the same materials of construction.

21. The device of claim 16, wherein the multi-electrode array comprises a first electrode and a second electrode, wherein the first electrode comprises material different from that of the second electrode.

22. The device of claim 16, wherein the multi-electrode array comprises a first electrode and a second electrode, wherein the first electrode has a substantially the same geometrical shape as that of the second electrode.

23. The device of claim 16, wherein the multi-electrode array comprises a first electrode and a second electrode, wherein the first electrode has a geometrical shape different from that of the second electrode.

24. The device of claim 1, wherein the sensor comprises multiple wires or wire bundle electrodes.

25. The device of claim 1, wherein the plurality of electrodes are incorporated into a subdural grid.

26. The device of claim 1, wherein the sensor comprises two or more discrete components, each of the discrete components comprising at least one of the plurality of electrodes.

27. The device of claim 26, wherein the discrete components comprise two or more of the following: a multi-electrode array; multiple wires or wire bundles; a subdural grid; and scalp electrodes.

28. The device of claim 1, wherein at least one of the plurality of electrodes is implanted near the central nervous system.

29. The device of claim 1, wherein at least one of the plurality of electrodes is implanted within the brain.

30. The device of claim 29, wherein at least one of the plurality of electrodes is implanted within the motor cortex of the brain.

31. The device of claim 1, wherein at least one of the plurality of electrodes is implanted at an extracranial site.

32. The device of claim 1, wherein at least one of the plurality of electrodes is implanted above the patient's scalp.

33. The device of claim 1, wherein at least one of the plurality of electrodes is configured to record signals from a plurality of neurons.

34. The device of claim 1, wherein the cells include one or more of nerve cells, muscle cells, organ cells, and tumor cells.

35. The device of claim 1, wherein each of the plurality of conductors is connected to one of the electrodes.

36. The device of claim 1, wherein at least one of the plurality of conductors is connected to more than one electrode.

37. The device of claim 1, wherein the connector assembly is relatively rigid.

38. The device of claim 1, wherein the connector assembly is relatively flexible.

39. The device of claim 1, wherein the connector assembly comprises a relatively rigid portion and a relatively flexible portion.

40. The device of claim 1, wherein the attachment member comprises one or more clearance holes to allow passage of an anchoring device.

41. The device of claim 40, wherein the anchoring device comprises a bone screw.

42. The device of claim 1, wherein the attachment member comprises a woven polyester cuff.

43. The device of claim 1, wherein the at least one signal communication port comprises an electrical contact.

44. The device of claim 1, wherein the at least one signal communication port comprises multiple signal communicator ports comprising electrical contacts.

45. The device of claim 1, further comprising an alignment device configured to align a connecting device in a single orientation to the connector assembly.

46. The device of claim 1, further comprising a controlled device.

47. The device of claim 1, further comprising an engagement member configured to connect the connector assembly to an external mating connector, wherein the engagement member is located at least partially beneath the surface of the patient's skin when the device is implanted in the patient.

48. The device of claim 1, wherein the electrical conduit is detachably connected to the connector assembly.

49. The device of claim 1, wherein the connector assembly comprises a flexible sheath configured to exit though the patient's skin when the device is implanted in the patient.

50. A neural access device for implanting in a patient comprising:
- a sensor comprising a plurality of electrodes to allow for chronic access of cells;
- an electrical conduit comprising a plurality of conductors, each conductor electrically connected to one or more of the electrodes;
- a connector assembly comprising:
  - a first portion configured to be placed above a surface of a patient's skin;
  - a second portion configured to be placed beneath the surface of the patient's skin;
  - an attachment member for securing the second portion beneath the surface of the patient's skin; and
  - at least one signal communication port configured to transport a signal to and/or from one or more of the electrodes, and to be placed external to the patient when the device is implanted in the patient
- an electrostatic discharge protector configured to protect the device from electrostatic discharge
- wherein the signal communication port is configured to transmit cellular activity detected from one or more of the electrodes and electrical signals to one or more of the electrodes
- wherein the cellular activity is detected from one or more of the electrodes and the electrical signals are transmitted to at least one of the one or more electrodes from which cellular activity is detected.

51. The device of claim 50, wherein the sensor is configured to detect multicellular signals emanating from the central nervous system.

52. The device of claim 50, wherein the sensor is configured to transmit electrical signals to the central nervous system.

53. The device of claim 50, wherein the plurality of electrodes are incorporated into a subdural grid.

54. The device of claim 50, wherein the at least one signal communication port comprises an electrical contact.

55. The device of claim 50, wherein the at least one signal communication port comprises multiple signal communicator ports comprising electrical contacts.

56. The device of claim 50, wherein the at least one signal communication port comprises an optical port.

57. The device of claim 50, wherein the at least one signal communication port comprises a first signal communication port comprising an electrical contact and a second communication port comprising an optical port.

58. The device of claim 50, wherein the signal communication port is configured to transmit cellular activity detected from one or more of the electrodes.

59. The device of claim 50, wherein the signal communication port is configured to transmit electrical signals to one or more of the electrodes.

60. The device of claim 50, further comprising an engagement member configured to connect the connector assembly to an external mating connector, wherein the engagement member is located at least partially beneath the surface of the patient's skin when the device is implanted in the patient.

61. The device of claim 50, wherein the electrical conduit is detachably connected to the connector assembly.

62. The device of claim 50, wherein the connector assembly comprises a flexible sheath configured to exit though the patient's skin when the device is implanted in the patient.

63. A neural access device for implanting in a patient comprising:
- a sensor comprising a plurality of electrodes to allow for chronic access of cells;
- an electrical conduit comprising a plurality of conductors, each conductor electrically connected to one or more of the electrodes;
- a connector assembly comprising:
  - a first portion configured to be placed above a surface of a patient's skin;
  - a second portion configured to be placed beneath the surface of the patient's skin;
  - an attachment member for securing the second portion beneath the surface of the patient's skin; and
  - at least one signal communication port configured to transport a signal to and/or from one or more of the electrodes
- an electrostatic discharge protector configured to protect the device from electrostatic discharge
- wherein the signal communication port is configured to transmit cellular activity detected from one or more of the electrodes and electrical signals to one or more of the electrodes
- wherein the cellular activity is detected from one or more electrodes and the electrical signals are transmitted to at least one of the one or more of the electrodes from which cellular activity is detected.

64. The device of claim 63, wherein the plurality of electrodes are incorporated into a subdural grid.

* * * * *

UNITED STATES PATENT AND TRADEMARK OFFICE
CERTIFICATE OF CORRECTION

PATENT NO.        : 7,647,097 B2                                               Page 1 of 1
APPLICATION NO.   : 11/014907
DATED             : January 12, 2010
INVENTOR(S)       : Flaherty et al.

It is certified that error appears in the above-identified patent and that said Letters Patent is hereby corrected as shown below:

Column 23, line 15: delete "of the"

Column 25, line 11: replace "though" with --through--

Column 25, line 38: delete "of the"

Column 26, line 21: replace "though" with --through--

Column 26, line 48: delete "of the"

Signed and Sealed this

Twenty-third Day of February, 2010

David J. Kappos
*Director of the United States Patent and Trademark Office*